United States Patent [19]

Nekrasov et al.

[11] Patent Number: 5,503,830
[45] Date of Patent: Apr. 2, 1996

[54] COMPOUNDS HAVING IMMUNOSTIMULATING ACTIVITY AND METHODS OF USE THEREOF

[75] Inventors: Arkady V. Nekrasov, Ravshan I. Ataullakhanov, Rem V. Petrov, Rakhim M. Khaitov, all of Moscow, Russian Federation

[73] Assignee: Petrovax, L.L.C., New York, N.Y.

[21] Appl. No.: 120,001

[22] Filed: Sep. 10, 1993

[51] Int. Cl.⁶ .................. A61K 39/385; A61K 39/39; C07D 243/06; C07D 243/04; C07D 243/02; C07D 243/08; C07D 403/06; C07D 231/04

[52] U.S. Cl. .................. 424/193.1; 424/280.1; 540/575; 540/553; 544/357; 544/296; 544/238; 548/313.7; 548/365.4

[58] Field of Search ............... 424/280.1, 193.1; 544/295, 296, 357, 238; 548/312.7, 313.7, 365.4; 540/575, 553; 526/263, 258

[56] References Cited

U.S. PATENT DOCUMENTS 4,927,931  5/1990  Molzahn et al. .................. 544/357

FOREIGN PATENT DOCUMENTS 153174  10/1966  Hungary.
420637   3/1974  U.S.S.R..
523908   8/1976  U.S.S.R..

OTHER PUBLICATIONS

Allison et al in "Vaccines: New Approaches to Immunological Problems" ed R. W. Ellis, 1992, Butterworth-Heinemann, pp. 431–449.

Allison et al (1991) Mol. Immunol. 28(3):279–284.
Gupta et al (1993) Vaccine 11(3): 293–306.
Zaharko et al (1984) Cancer Treat. Rep. 68(10):1255–1264.
Lovgren et al (1991) Mol. Immunol. 28(3):285–286.
English Translations of SU420637.
English Translation of SU523908.

*Primary Examiner*—Kay K. A. Kim
*Attorney, Agent, or Firm*—Duane, Morris & Heckscher

[57] ABSTRACT

Polymeric compounds comprising subunits of the following formulas

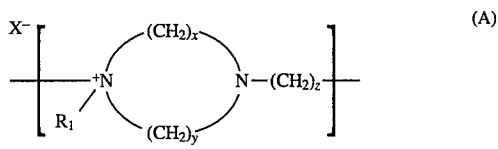

(A)

and

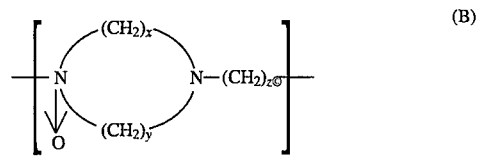

(B)

wherein $R_1$, X, x, y, z, x', y' and z' are as defined in the application. The polymeric compounds are capable of stimulating the immune response system of animals, including humans. The polymeric compounds are useful also in the manufacture of medicaments, including vaccines, for the prophalaxis and treatment of conditions requiring an enhanced immune response.

56 Claims, 9 Drawing Sheets

SN, ADDED TO TC MEDIUM, STIMULATED MIGRATION ACTIVITY OF MOUSE MACROPHAGES

SN, INJECTED IN MICE, RESULTED IN AN ENHANCED MACROPHAGE MIGRATION

BEHAVIOR OF RATS AFTER 14 INJECTIONS OF SN-100

COMPOUNDS HAVING IMMUNOSTIMULATING ACTIVITY AND METHODS OF USE THEREOF

FIELD OF THE INVENTION

The present invention relates to substances capable of stimulating the immune system.

BACKGROUND

In the ongoing fight against disease, new and improved methods for stimulating the immune system are continually being sought. Augmentation of the immune system is required, as it is not always possible to have an immunity before contracting a disease, and it may be too late to react successfully against the disease once the symptoms have manifested.

Accordingly, significant amounts of research have been dedicated to establishing and finding substances which will give an advantage against an infection. Prime amongst these is the use of vaccines but, unfortunately, the substances against which it is desired to generate an immunity do not always prove immunogenic, or are only weakly immunogenic and cannot be used to generate an adequate immune response.

Accordingly, attention has focused on synthetic substances to promote a response against disease, and various classes of substance have been found. Amongst these classes are the adjuvants, the immune stimulants and the carriers.

Adjuvants are used to boost an immune response against a vaccine, and may even be used to stimulate an immune response against an otherwise non-immunogenic antigen. A typical example of an adjuvant is Freund's Complete Adjuvant (FCA). This adjuvant works very well in animals, but leads to significant swelling and pain in humans, and cannot be used. There exist adjuvants which can be used in human medicine, such as aluminium salts, but the choice is somewhat restricted, and the available adjuvants tend not to be particularly effective.

Immune stimulators are those compounds which stimulate the immune system, even in the absence of suitable antigenic material. Many such substances have been identified, but such compounds tend to be toxic, and cannot easily be catabolized. An example of such a substance is polyvinylpyrrolidone.

Carrier substances are generally proteins which are complexed or conjugated with an antigen or hapten and, by virtue of the association with the antigen or hapten, can cause an immune response to be generated where otherwise there would be none. The problem with this system is that the carrier protein must be so selected as not to be antigenic itself.

It will be appreciated, therefore, that there is considerable demand for new substances which can successfully be used in any of the above categories. We have now discovered that a series of quaternary salts of polyheterocyclic compounds is useful in all of the above categories.

SUMMARY OF THE INVENTION

The present invention is directed to a polymer comprising subunits of the following formulae

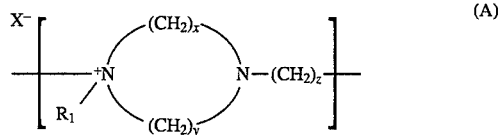

and

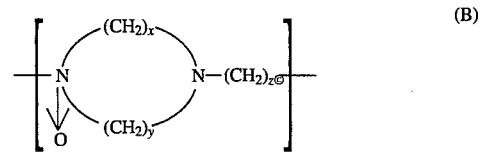

wherein $X^-$ is a pharmaceutically acceptable anion; $R_1$ is substituted or unsubstituted $C_{1-16}$ alkyl, substituted or unsubstituted $C_{1-16}$ alkenyl or substituted or unsubstituted $C_{1-16}$ alkynyl, said $R_1$ substituents being selected from the group consisting of hydroxy, amino, substituted or unsubstituted $C_{6-10}$ aryl, $C_{1-16}$alkyamino, di-$C_{1-6}$-alkylamino, carboxy, alkoxy carbonyl, carboxamido, cyano, $C_{1-6}$-alkoxy and halogen, aryl group substituents being selected from the group consisting of hydroxy, amino, $C_{6-10}$ aryl, $C_{1-16}$-alkylamino, di-$C_{1-6}$-alkylamino, carboxy, alkoxy carbonyl, carboxamino, cyano, $C_{1-6}$-alkoxy, halogen, $C_{1-6}$ alkyl and $C_{1-6}$ haloalkyl; x+y is an integer from 3 to 5; z is an integer from 1 to 3; x'+y' is an integer from 3 to 5 and may be the same or different as x+y; z' is an integer from 1 to 3 and may be the same or different as z; and the ratio of A to B is from 1:9 to 9:1. The present invention is also directed to a method of stimulating the immune response system of animals, including humans, comprising administering to said animal a polymer in an amount effective to stimulate said immune response system.

DETAILED DESCRIPTION OF THE INVENTION

The present invention provides a polymer consisting essentially of the subunits

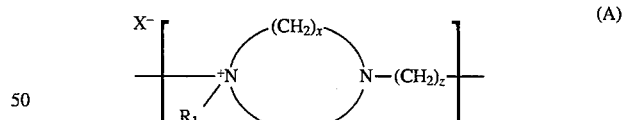

and

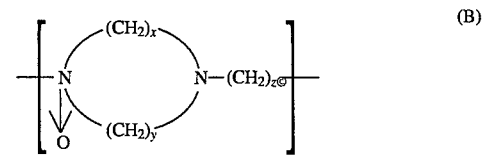

wherein X represents a pharmaceutically acceptable anion; $R_1$ represents a $C_{1-6}$ alkyl, a $C_{1-16}$ alkenyl or a $C_{1-16}$ alkynyl group, and is optionally substituted by one or more substituents selected from hydroxy, amino, $C_{6-10}$ aryl, $C_{1-6}$ alkylamino, di-$C_{1-6}$-alkylamino, cyano, $C_{1-6}$-alkoxy groups and halogen atoms, said aryl groups being optionally further similarly substituted, said substituents also including $C_{1-6}$ alkyl and $C_{1-6}$ haloalkyl groups, provided that any further aryl substituents are not further substituted by aryl groups, and wherein said carboxyl groups are optionally amidated or esterified;

x+y=3 to 5; z=1 to 3; x'+y'=3 to 5 and may be the same or different as x and y; z'=1 to 3 and may be the same or different as z; and the ratio of A to B is from 1:9 to 9:1.

The compounds of the present invention have been found to provide significant activity as adjuvants, carriers and immune stimulators. In trials, significant protection against lethal doses of disease organisms has been found in mice and chickens, for example, using only a prophylactic dose of the compound.

Accordingly, the present invention also provides the compounds defined above for use in therapy, and the use of compounds of the invention in the manufacture of medicaments, including vaccines, for the prophylaxis and treatment of conditions requiring an enhanced immune response.

A probable reason for the action of the compounds of the invention is that they appear to be able to stimulate mitogenesis, particularly phases I and II. Although the compounds of the invention do not appear to stimulate the production of interleukin, the stimulation of the production of interleukin-2 receptors can be noted. The mitogenic effect of the compounds of the invention is particularly noted in macrophages and, to a lesser extent, in lymphocytes.

While the precise nature of the mitogenic stimulation of the compounds of the invention is not known, passage of calcium ions across the cell membrane increases in the presence of the compounds. Association with a number of transmembrane proteins appears to result in the creation of calcium channels, and this may account for the observed mitogenesis.

Possibly as a result of their mitogenic activity, the compounds of the invention possess superior qualities as immune stimulants and adjuvants and, because they have reactive side groups, can also serve as carriers. In addition, the compounds of the invention exhibit good antitumor activity.

Further, the compounds of the present invention do not exhibit any immunogenic activity in themselves, and are non-toxic. Another advantage of the compounds of the present invention is that they can be catabolized into nontoxic products which can be easily excreted.

In the formula given above, it is preferred that the pharmaceutically acceptable anion is selected from halogen atoms, particularly chlorine, bromine or iodine.

x and y preferably total 4, as do x' and y' and it is particularly preferred that each of x, y, x' and y' is 2. Likewise, it is preferred that z is also 2. However, compounds of the present invention may also include such heterocyclic rings as imidazolidine, pyrazolidine and homopiperazine, for example, Preferred meanings for $R_1$ are $C_{1-16}$ alkyl and $C_{1-16}$ hydroxyalkyl. Carboxy-$C_{1-5}$ alkyl is also preferred and, when the carboxyl group is esterified or amidated, then preferred esters are $C_{1-4}$ alkoxy esters, while preferred amidating groups are $NH_2$, $NHNH_2$, $NH(CH_2)_{1-10}$, and $NH(CH_2)_{1-10}NH_2$.

The size of the polymer may be selected as desired, and may also be the result of the conditions used to prepare the compound. However, as a general rule, the total amount of sub-units is preferred to be between the limits of 310 and 2000.

Although many ratios of the sub-units of the polymers of the invention may be employed, it is generally preferred that the ratio of A:B is not lower than 2:8. It will also be appreciated that, even where the ratio of subunits is 1:1, it is extremely unlikely that each subunit will be alternating with the other, and that it is most likely that groups of each type of sub-unit would be observed throughout the molecule.

Use of the compounds of the present invention is not limited to humans, and the compounds may be used in all fields of veterinary practice, particularly mammalian. Owing to the fact that the compounds of the invention are capable of general stimulation of the immune system, as well as being able to act in both the capacity of adjuvant and carrier, then their use is not limited to any specific type of disease. Accordingly, use of the compounds of the invention extends not only to microorganisms, such as bacteria, and viruses, such as influenza, but also to cancerous growths. Essentially, the compounds of the invention may be used in any circumstance where an immune response is required, or where some form of disease needs to be fought, thereby to augment the body's natural response, if any exists.

Examples of bacterial infections include salmonellosis and cholera, and administration of a prophylactic dose of a compound of the invention is sufficient to prevent death from what would otherwise be a lethal quantity of the microorganism.

Likewise, compounds of the invention are capable of protecting against viral infections, such as Newcastle disease virus in chickens, and have been found to be particularly useful in the prophylaxis and treatment of helminth infestations, both in the presence and in the absence of helminth antigens.

The compounds of the present invention may be synthesized in any suitable manner. For example, USSR Inventor's Certificate Nos. 420637 and 523908 disclose suitable methods for the manufacture of poly-1,4-ethylenepiperazine-N-oxides. The initial poly-1,4-ethylenepiperazine may be prepared by the polymerization of diazabicyclo[2.2.2]octane, using the well-documented living chain process. Subsequently, the polymer may be oxidized at ambient or raised temperatures, such as up to about 200° C., in an alcoholic or mildly acidic aqueous solution of hydrogen peroxide. Finally, the substituent $R_1$ may be added by reaction with the N-oxide in an alcoholic solution of the appropriate compound. For example, a solution of bromoacetic acid will give a bromine anion and a carboxymethyl group as $R_1$.

The compounds of the present invention may be administered in any suitable manner to achieve the desired results. It will be appreciated that administration will vary according to the type of activity that is desired. For example, if immune stimulation is required, then a solution of the compound of the invention may be adminstered by injection, and it has been found that the intraperitoneal route is generally superior to the subcutaneous route. The compounds of the invention may also be administered orally, but this can lead to considerable wastage owing to the larger quantities that must be administered. If the compounds of the invention are used as adjuvants in vaccines, then they may be incorporated in the vaccine in any suitable proportion, and suitable doses may vary, for example, from 10 μg to 100 mg, preferably from 100 μg to 50 mg, especially from 1 mg to 30 mg.

When used as a carrier in a vaccine, similar considerations apply, including amounts of substance. In addition, similar quantities of compounds of the invention may also be used for immune stimulation and antitumor treatments.

The administration forms of the compounds of the present invention may be any that is suitable, and can vary from simple saline and other aqueous solutions, through to complex administration forms, such as gelatin capsules.

In general, administration forms may include any suitable additives, such as surface active agents, flavorings, emulsifiers, preservatives, thickeners and other therapeutic agents.

The following Examples serve to illustrate the preparation of compounds of the invention and experiments to demonstrate their activity, and do not serve to limit the present invention in any way.

EXAMPLE 1

Figure 1:
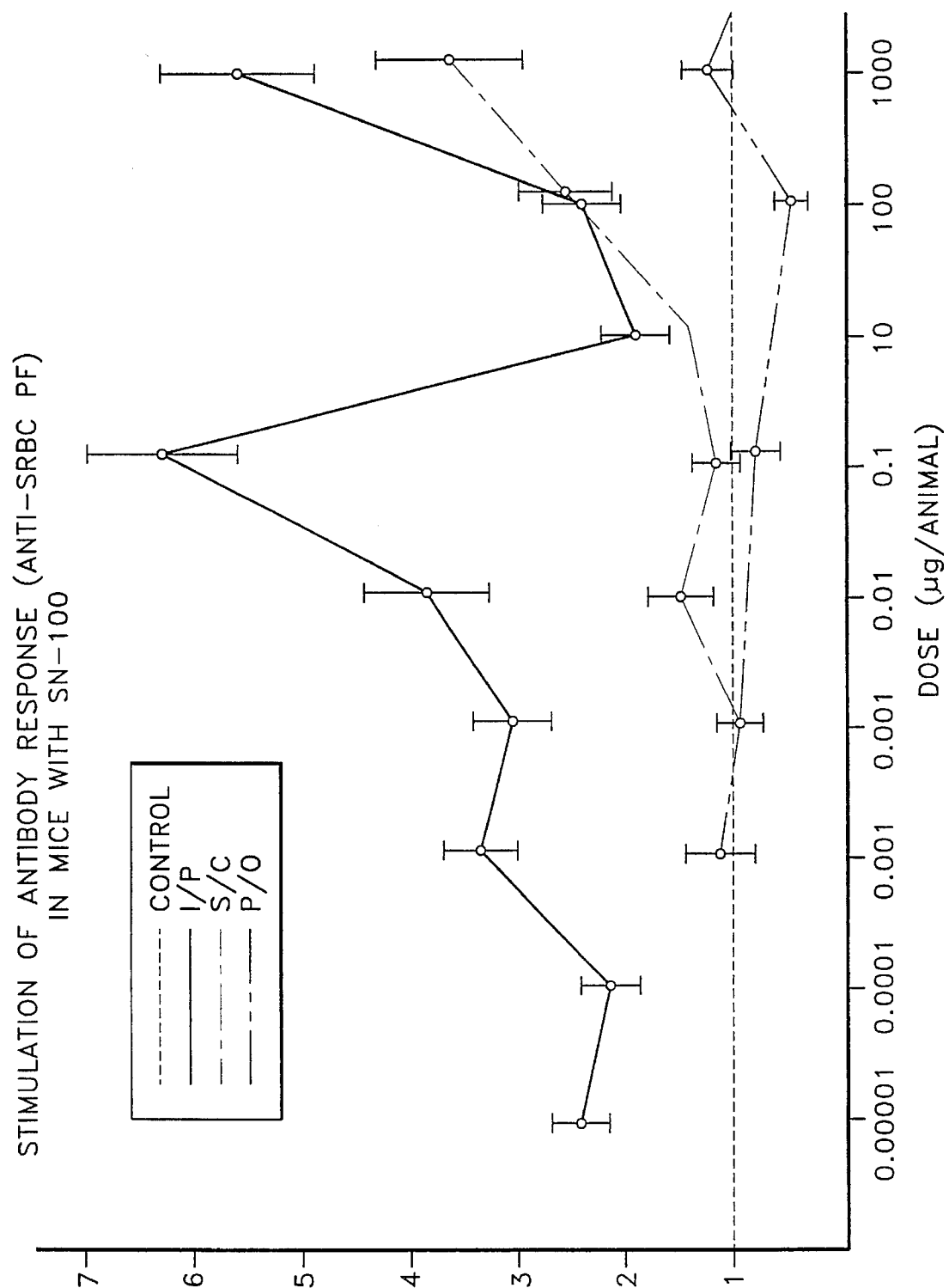
FIG. 1 presents the stimulation of antibody response in mice using SYNPOL-100.

5 g of poly-1,4-ethylenepiperazine (Mw 35000, n=310) was dissolved in 250 ml of 1% acetic acid solution. At 2°–4° C. and permanent agitation we added 4.6 ml of 30% $H_2O_2$ solution. Oxidation lasted for 48 h. Then ultrafilter cleaning and lyophilic evaporation were performed. Poly-1,4-ethylenepiperazine N-oxide obtained was dissolved in 125 ml of methanol and 16.5 g of bromacetic acid was added. The reaction of poly-N-oxide alkylation was performed at 25° C. temperature during 14 h. The solvent was evaporated in vacuum. The deposit was dissolved in water, dialyzed against water and lyophilized. We got the following compound which we shall refer to hereinafter as SYNPOL (the ratio of A:B being 0.35:0.65, as shown):

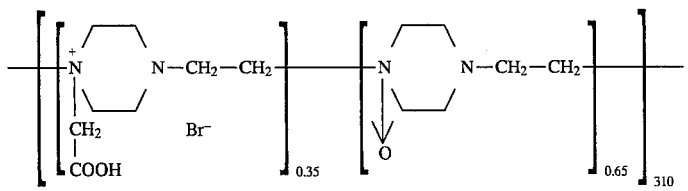

The yield was 95%. Oxidation ratio was estimated by choromometric titration methods and by the ratio of integral intensities of PMR-spectrum bands in region 2.5–4.5 m.d. Oxidation ratio amounted to z=0.65n. Alkylation ratio was determined by IR-spectra (1735 cm$^{-1}$ band) and PMR-spectra (2.5–4.5 m.d. region) and accounted for q=0.35n.

Element analysis data: C6.7H13.05O1.35N2Br0.35 Found, %: C 46.91 H 7.75 N 16.30 Calculated, %: C 47.00 H 7.63 N 16.37

EXAMPLE 2

5 g of poly-1,4-ethylenpiperazine (Mw 225000, n=2000) was dissolved in 250 ml of 1% acetic acid solution. At 2°–4° C. and permanent agitation we added 6.0 ml of 30% $H_2O_2$ solution. Oxidation lasted for 28 h. Then ultrafilter cleaning and lyophilic evaporation were performed. Poly-1,4-ethylenpiperazine N-oxide obtained was dissolved in 125 ml of methanol and 30.0 ml of ethylenbromhydrine was added. The reaction of poly-N-oxide alkylation was performed at 25° C. during 24 h. The solvent was evaporated in vacuum, the deposit was dissolved in water, dialyzed against water and lyophilized. We got the compound with the following formula:

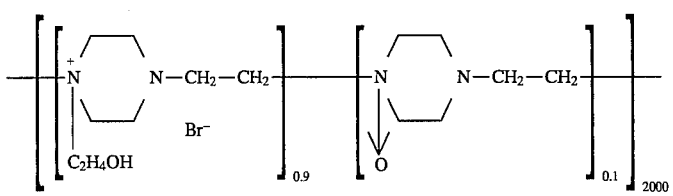

The yield was 95%. Oxidation ratio was estimated by choromometric titration methods and by the ratio of integral intensities of PMR-spectrum bands in region 2.5–4.5 m.d. Oxidation ratio amounted to z=0.10n. Alkylation ratio was determined by IR-spectra (1735 cm$^{-1}$ band) and PMR-spectra (2.5–4.5 m.d. region) and accounted for q=0.90n.

Element analysis data: C7.8H16.5ON2Br0.90 Found, %: C 41.30 H 7.40 N 12.31 Calculated, %: C 41.30 H 7.30 N 12.38

EXAMPLE 3

1 g of poly-1,4-ethylenepiperazine (Mw 110000, n=1000) was dissolved in 50 ml of 1% acetic acid solution. At 2°–4° C. and perment agaitation we added 3.0 ml of 30% $H_2O_2$ solution. Oxidation lasted for 56 h. Then ultrafilter cleaning and lyophilic evaporation were performed. Poly-1,4-ethylenepiperazine N-oxide obtained was dissolved in 25 ml of methanol and 4.2 ml of ethyl bromide was added. The reaction of poly-N-oxide alkylation was performed at 20° C. during 6 h. The solvent was evaporated in vacuum, the deposit was dissolved in water, dialyzed against water and lyophilized. We got the compound of the following formula:

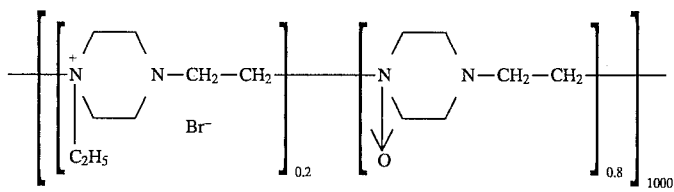

The yield was 90%. Oxidation and alkylation ratio were estimated as described in Example 1. z=0.8n, q=0.2n.

Element analysis data: C6.4H130N2Br0.20 Found, % : C 51.21 H 8.71 N 18.63 Calculated, %: C 51.27 H 8.68 N 18.69

In Table 1 there are other examples of poly-1,4-ethylene-piperazine compounds; their structure, physical and chemical characteristics and reaction conditions (compounds 4–36) are shown.

Spleen AGC were determined by local haemolysis in agar (Erne method). Antibody titres against specific protein antigens were estimated by ELISA. Adjuvant efficiency was measured as the relation of AGC number to that in control animals at simultaneous injection of antigens and polymers.

Preparation doses varied 1–1000 mg/kg/mouse at intraperitoneal and subcutaneous preparation injection.

TABLE 1

| N Hal | $R_1$ | $R_2$ | n | q/n | z/n | Alkylation reaction conditions T° C. | t,h |
|---|---|---|---|---|---|---|---|
| 4. Cl | $C_2H_5$ | — | 350 | 0.9 | 0.1 | 40 | 32 |
| 5. Br | $H_3$ | — | 2000 | 0.9 | 0.1 | 25 | 15 |
| 6. Br | $C_4H_9$ | — | 500 | 0.5 | 0.5 | 40 | 38 |
| 7. Br | $C_6H_{13}$ | — | 1000 | 0.4 | 0.6 | 40 | 70 |
| 8. Br | $C_16H_{33}$ | — | 500 | 0.2 | 0.8 | 40 | 200 |
| 9. I | $C_6H_{13}$ | — | 310 | 0.8 | 0.2 | 40 | 14 |
| 10. Br | $(CH_2)_3OH$ | — | 1800 | 0.8 | 0.2 | 25 | 12 |
| 11. Br | $(CH_2)_4OH$ | — | 1000 | 0.6 | 0.4 | 40 | 35 |
| 12. Br | $(CH_2)_{16}OH$ | — | 325 | 0.3 | 0.7 | 40 | 70 |
| 13. Br | $(CH_2)COR_2$ | OH | 2000 | 0.35 | 0.65 | 25 | 14 |
| 14. Br | $(CH_2)_2COR_2$ | OH | 1000 | 0.5 | 0.5 | 25 | 24 |
| 15. Br | $(CH_2)_3COR_2$ | OH | 500 | 0.3 | 0.7 | 40 | 48 |
| 16. Br | $(CH_2)_4COR_2$ | OH | 825 | 0.3 | 0.7 | 40 | 58 |
| 17. Br | $(CH_2)_5COR_2$ | OH | 400 | 0.2 | 0.8 | 40 | 70 |
| 18. Br | $(CH_2)COR_2$ | $OCH_3$ | 2000 | 0.4 | 0.6 | 25 | 12 |
| 19. Br | $(CH_2)_2COR_2$ | $OCH_3$ | 1000 | 0.35 | 0.65 | 25 | 24 |
| 20. I | $(CH_2)_5COR_2$ | $OCH_3$ | 700 | 0.3 | 0.7 | 40 | 48 |
| 21. Br | $(CH_2)COR_2$ | $OC_2H_5$ | 1000 | 0.5 | 0.5 | 25 | 24 |
| 22. Br | $(CH_2)_2COR_2$ | $OC_2H_5$ | 700 | 0.4 | 0.6 | 25 | 48 |
| 23. Br | $(CH_2)_3COR_2$ | $OC_2H_5$ | 900 | 0.35 | 0.65 | 40 | 80 |
| 24. Br | $(CH_2)COR_2$ | $OC_4H_9$ | 1000 | 0.4 | 0.6 | 40 | 52 |
| 25. Br | $(CH_2)COR_2$ | $NHNH_2$ | 2000 | 0.4 | 0.6 | 25 | 28 |
| 26. Br | $(CH_2)_2COR_2$ | $NHNH_2$ | 600 | 0.3 | 0.7 | 25 | 40 |
| 27. Br | $(CH_2)COR_2$ | $NH(CH_2)NH2$ | 800 | 0.9 | 0.1 | 25 | 54 |
| 28. Br | $(CH_2)_2COR_2$ | $NH(CH_2)NH2$ | 1500 | 0.4 | 0.6 | 40 | 43 |
| 29. Br | $(CH_2)COR_2$ | $NH(CH_2)_2NH_2$ | 1000 | 0.35 | 0.65 | 40 | 45 |
| 30. Br | $(CH_2)COR_2$ | $NH(CH_2)_3NH_2$ | 800 | 0.3 | 0.7 | 40 | 50 |
| 31. Br | $(CH_2)COR_2$ | $NH(CH_2)_4NH_2$ | 1500 | 0.2 | 0.8 | 40 | 68 |
| 32. Br | $(CH_2)COR_2$ | $NH(CH_2)_6NH_2$ | 2000 | 0.2 | 0.8 | 40 | 70 |
| 33. Br | $(CH_2)COR_2$ | $NH(CH_2)_8NH_2$ | 750 | 0.2 | 0.8 | 40 | 84 |
| 34. Br | $(CH_2)COR_2$ | $NH(CH_2)_{10}NH_2$ | 450 | 0.4 | 0.6 | 40 | 89 |
| 35. Br | $(CH_2)_5COR_2$ | $NH(CH_2)NH_2$ | 2000 | 0.4 | 0.6 | 40 | 28 |
| 36. Br | $(CH_2)_2COR_2$ | $NH(CH_2)_2NH2$ | 1000 | 0.5 | 0.5 | 40 | 18 |

EXAMPLE 4

Immunomodulating Activity and Acute Toxicity

The immunomodulating activity of these compounds was determined by a number of antibody generating cells (AGC), being formed on the 4–7th day in mouse spleen. Mice had been immunized by either sheep red blood cells or protein antigens (cholera toxin B-subunit, anthrax toxin) and simultaneously injected by high molecular weight compounds.

The acute toxicity was determined in mice, rats and guinea-pigs. 5–8% compounds solutions were injected subcutaneously or intraperitoneally once or twice. LD 50 was determined according to standard method. Each group consisted of 10–20 animals.

The results of testing are presented in Table 2.

TABLE 2

Immunomodulating Activity and Acute Toxicity Investigation

| Compounds | Polymerization Ratio | Stimulation Coefficient AGC/AGC | Acute Toxicity LD50 g/kg weight |
|---|---|---|---|
| 1 | 310 | 2.9 | 2.1 |
| 2 | 2000 | 9.5 | 0.25 |
| 3 | 1000 | 3.4 | 1.9 |
| 4 | 350 | 3.2 | 0.3 |
| 5 | 2000 | 8.0 | 0.2 |
| 6 | 500 | 4.1 | 1.8 |
| 7 | 1000 | 4.8 | 1.4 |
| 8 | 500 | 5.4 | 1.8 |
| 9 | 310 | 3.7 | 0.25 |
| 10 | 2000 | 10.2 | 0.2 |
| 11 | 1000 | 9.5 | 0.6 |
| 12 | 325 | 3.3 | 1.7 |
| 13 | 2000 | 12.0 | 1.4 |
| 14 | 1000 | 9.0 | 1.45 |
| 15 | 500 | 3.7 | 1.8 |
| 16 | 825 | 3.5 | 1.6 |
| 17 | 400 | 3.2 | 2.8 |
| 18 | 2000 | 11.0 | 1.2 |
| 19 | 1000 | 8.0 | 1.3 |
| 20 | 700 | 4.5 | 1.7 |
| 21 | 1000 | 8.4 | 1.5 |
| 22 | 700 | 3.8 | 2.1 |
| 23 | 900 | 3.7 | 1.0 |
| 24 | 1000 | 7.6 | 1.2 |
| 25 | 2000 | 10.6 | 0.9 |
| 26 | 600 | 4.1 | 1.6 |
| 27 | 800 | 3.7 | 0.5 |
| 28 | 1500 | 11.0 | 0.8 |
| 29 | 1000 | 9.4 | 0.85 |
| 30 | 800 | 4.3 | 1.7 |
| 31 | 1500 | 5.3 | 1.2 |
| 32 | 2000 | 6.3 | 1.1 |
| 33 | 750 | 4.8 | 1.4 |
| 34 | 450 | 3.8 | 1.3 |
| 35 | 2000 | 12.0 | 0.85 |
| 36 | 1000 | 8.4 | 0.9 |

EXAMPLE 5

The Investigation of Antivirus Activity Was Performed on Chickens at the Poultry Farm The influence of copolymer of ethylenepiperazine N-oxide and N-hydroxypropylethylenepiperazinium bromide (Mw 120000) on immunity formation against Newcastle disease virus, on preservation and chicken mass increase was studied.

00,000 chickens were treated. Chickens were immunized by aerosol. Specific antibodies were determined in blood serum by haemoagglutination delay reaction. Chickens were constantly observed, weighed and kept. The high-grade immunity serological control was performed.

The Newcastle disease virus immunity study showed that on 21st day after immunization antihaemagglutinin titre 4-fold exceeded control group titre. In preparation treated groups 65% chicken lethality decrease and 30% body weight increase as compared to control group were revealed.

Similar results were obtained at the testing of poly-1,4-ethylenepiperazine derivatives: compounds 4–8, 11–17, 21–27, 29–34 (Table 1).

EXAMPLE 6

Antibacterial Activity (Compounds 3, 4, 10–12, 18–22 in Table 1)

Antibacterial activity of these compounds was studied in the experiments on the non-specific mouse resistance to *Salmonella typhimurium* and *Streptococococcus pneumoniae* infection.

We used (CBAxC57B1/6)F mice. 0.05–50 mg/kg of preparations were injected intraperitoneally and subcutaneously at 96, 72 and 48 h before infection. Animal lethality was recorded during 21 h after infection. This method allows to evaluate tile survival and immune status.

The results of the experiments carried out are performed in Table 3 (preparation 13 in Table 1).

TABLE 3

| Group No. | Animal No. | Infection Dose (mg/kg/mouse) | Preparation Dose (mg/kg) | Injection Terms | Animal Lethality % |
|---|---|---|---|---|---|
| 1 | 10 | Streptococcus pneumonia T-3, 10 mg/kg | — | | 100 |
| 2 | 10 | Streptococcus pneumonia T-3, 10 mg/kg | 5.0 | 48 h before inj. s/c | 38 |
| 3 | 10 | Streptococcus pneumonia T-3, 10 mg/kg | 12.5 | 48 h before inj. s/c | 50 |
| 4 | 50 | S. typhimurium 415.5 10 mg/kg | — | | 92 |
| 5 | 40 | S. typhimurium 415.5 10 mg/kg | 0.05 | i/p; 96 h before inj. | 7.8 |
| 6 | 30 | S. typhimurium 415.5 10 mg/kg | 0.5 | i/p; 96 h before inj. | 0 |
| 7 | 30 | S. typhimurium 415.5 10 mg/kg | 0.05 | i/p; 72 h | 8.6 |
| 8 | 30 | S. typhimurium 415.5 10 mg/kg | 5.0 | " | 0 |
| 9 | 20 | S. typhimurium 415.5 10 mg/kg | 25.0 | s/c; 96 h | 20 |

The simlar results were obtained under poly-1,4-ethylenepiperazine derivatives testing (compounds 3, 4, 10–12, 18–22 in Table 1).

As we see from the data presented in Table 3, poly-1,4-ethylenepiperazine derivatives possess significant protective effect against developing infection. This may be due to the activation of digesting capacity of mouse peritoneal macrophages.

EXAMPLE 7

Influence on Chicken Protection Against Mixed Infection (Pullorosis and Colibacteriosis) Study at the Poultry Farm Medical and prophylactic chicken treatment by preparation (ex. 3) against mentioned infections was performed by aerosol. 200,000 chickens were treated twice by 3–5 mg/kg preparation. The interval between two treatments is 7 days. The following results were obtained.

When treated by immunostimulators chickens had no pullorosis and colibacteriosis symptoms. The pathoanatomical dissection of chickens killed for diagnostic examination showed 5.2% pathognomonic changes in preparation treated ones. The control group showed 29% pathognomonic changes.

The preservation of chickens was 95% and 60% correspondingly. The average chicken weight increase per day was 30 g and 17 g correspondingly.

The similar results were obtained with compounds 1–5, 9–12, 16–18, 27–30, 34–36.

Besides chicken preservation and weight increase the antibiotic usage was shortened. This allows us to obtain ecologically clean chicken production.

SYNPOL is a dry white material and is stable for up to six months at 4° C. and is soluble in aqueous solution of 0.9% NaCl. The material dissolves at room temperature over one hour with shaking for one hour (up to 20 mg/ml). Before administration, the solution is sterilized by filtration (Millipore 0.2 nm). The solution is stable for 2 months at −20° C.

Doses (immunoadjuvant and prophylactic) Mice: 0.1–1.0 mg/mouse subcutaneously or intraperitoneally Lambs: 2.0–10.0 mg/10–20 kg Lamb subcutaneously Sheep: 10.0–20.0 mg/50–70 kg Sheep subcutaneously Chickens: 3.0 mg/bird orally (drinking water)

The effects of SYNPOL are prolonged. Optimum dosing is 2 administrations with a two-week interval.

Aerosol application is used and is sometimes more convenient with birds. An aerosol of a 0.3% solution of Synpol is sprayed into a special box containing the birds (1 ml per a one cubic meter sized box). Approximately 100 chickens can be treated in one application in a one cubic meter sized box.

It is recommended that the first treatment of chickens is at age of 5 days and second at age of 19-20 days.

EXAMPLE 8

The Trials

The results of the trials on lamb, calves and chickens show that SYNPOL (Sn) has a prophylactic and therapeutic activity against various contagious diseases in farm animals.

Scientific Research Veterinary Institute of Uzbekistan (Village Tailyak of the Samarkand Region)

The immune-stimulating and protective effect of the Synpol in 16 lambs aged one month, during their experimental infection with the virus of infections rhinotracheitis has been demonstrated. In the control group of the four infected lambs without SYNPOL there was severe clinical rhinotracheitis. It was also noted that all the infected lambs had a serious decline of the immunity indexes (decline in the number of leucocytes and T-lymphocytes) and one out of four lambs died. The experimental group of 16 lambs, which had received SYNPOL (5 mg per head, hypodermic injection), and had been infected with the same dose of virus, had showed much weaker clinical symptoms of tracheitis and the immunal indexes did not fall below the normal (there were no deaths).

Two collective live stock farms in Pakhtchitaiski region of Uzbekistan

SYNPOL has been used as a prophylactic against respiratory and gastric diseases of the newly born calves. At these farms up to 30–50% of calves aged up to 25–30 days have been getting respiratory and gastric diseases, the majority of the calves died, the approximate death range is 10–12% of the whole calf population. In the first few days after the birth, SYNPOL was injected to 653 calves. During the period of a month, the calves that had received Synpol had a much lower frequency of respiratory and gastric diseases. The death rate fell to 5% of the population that had been injected with Synpol.

The Live Stock Collective Farm "Bolshevik" of the Belgorod Region.

Bronchial pneumonia was successfully treated by SYNPOL in 110 calves, aged 1–5 months, (60–100 kg of live weight). The similar group of calves, which was not receiving Synpol, was used as the control group. During 30 days of observation, 45% of the calves in the control group were infected by the bronchial pneumonia, 8% of the calves from the main population died. Of group of 110 calves that were receiving SYNPOL (in aerosol, 30 mg per head), only 7 calves (6%) had caught the disease and there were no deaths.

The All-Union Institute of the Experimental Veterinary, in the Department of Contagious Diseases of Birds The experiments on prophylactic and medical effects on contagious diseases in birds with polyoxidonium, were carried out. It has been shown that the aerosol use (1.5 mg per head), as well as the per-oral one (2.5 mg per head) in the first days of the chickens lives, protects them from the future infection with the lethal doses of pathogens of pullorose-typhus and micoplasmosis.

In the conditions of a livestock poultry farm, Synpol was used for prophylactics and medical care of the contagious diseases of the chickens. The trials were carried out on the following poultry farms in various regions of the USSR:

Poultry farm in the name of 60th Anniversary of the Formation of the USSR, Ivanovskaya region;

Poultry farm "Bashkirskaya", the Ufimski region, Bashkiria;

Poultry farm "Besharik", the Ferganskaya region of Uzbekistan;

Poultry farm "Samarkandskaya", the Samarkank region, Uzbedistan.

In all the cases where SYNPOL has been used, the spread of the infections, typical for that farm has been prevented, (the "control" were those chickens that lived in the other departments of the same poultry farm.) The death level of the chickens declined from 7.1% of the whole population to 2.0–2.5%. The broiler chickens put on more weight with SYNPOL. The chickens, that received SYNPOL twice (1.5–2.5 mg per head on the 3rd and 7th days of their lives), had at the end of the 2nd month of their life a weight that was 50–250 grams more than the "control" chickens.

The Livestock Collective Farm "Safonovski" of the Ramenski region, Moscow zone.

The 1 to 5 day old piglets were intramuscularly injected with the dose of 10 or 50 mg per head, for the prophylactics of the infection. On the whole, 294 heads were injected with SYNPOL. The "control" was the group of 129 similar piglets. The effect of SYNPOL was detected by the preservation of the population. In the "control" group of 129 piglets, 35 died (27%). In the experimental group of 294 piglets that have received the SYNPOL, 34 piglets died (14%).

Large Animals

Use of Synpol to Treat Sheep Infested with Dictiokaullesus and Fasciollus, Piroplasmosus.

SYNPOL was innoculated subcutaneously in the neck, 25–50 mg/sheep two times with a 72 hour interval.

Haematological analysis of piroplasmosis was made. The number and survival of helminths were made in dictiokaullesus and fascidesus and were compared with the control group of animals.

Results:

1. Survival and number of helminths (dictiokaullesus and fascioullesus) in 50 infested sheep treated with SYNPOL declined by 70%.

2. Protection from infestation was achieved in 60% of a trial group of 100 sheep. All the control sheep (100) died from infestation.

Summary of the Experimental Study of Immunomodulating, Pharmacological and Toxic Effects of SYNPOL SYNPOL is a synthetic biodegradable high polymer with M.W. of 100–120 kD, 60% oxidation degree and alkalinizing degree of 15–20%. It is a white hakeslike, well soluble in water and saline substance; pH 5.5.

SYNPOL pharmacological activity 1. corrects an immune response in immunodeficient mice;
2. prevents animals death from acute infection under prophylactic and therapeutic usage;
3. increases specific immunogenicity of vaccines;
4. manifests an antitumor activity;
5. protects animals against the toxic effect of chemicals;
6. protects the animal cells against cytotoxic action.

Recommended therapeutic dose for clinical use is 0.25 mg/kg. Recommended administration schedule is once a week, subcutaneously.

Wide range of the pre-clinical studies of SYNPOL has been carried out according to the requirements of the Pharmacological Committee of the USSR Ministry of Public Health.

The study of acute toxicity at parenteral administration in mice revealed SYNPOL to be of the class of practically non-toxic compounds. LD/50 in mice injected intraperitoneally was 1.476+/–0.073 g/kg. Death of animals was observed beginning since 11–14 days only. Histological examination showed that the death of animals treated with the toxic doses of SYNPOL was a result of the kidney injury.

Immunomodulating, pharmacological, general toxic, mutagenic and teratogenic activities of SYNPOL have been studied on the following animals:

410 Wistar rats,
7490 (CBA*C57B1/G)F1 mice,
290 CBA mice,
200 C57B1/6 mice,
40 Nu/Nu mice,
80 guinea pigs,
34 rabbits.

Table 4 lists the used tests.

EXAMPLE 9

Figure 2:
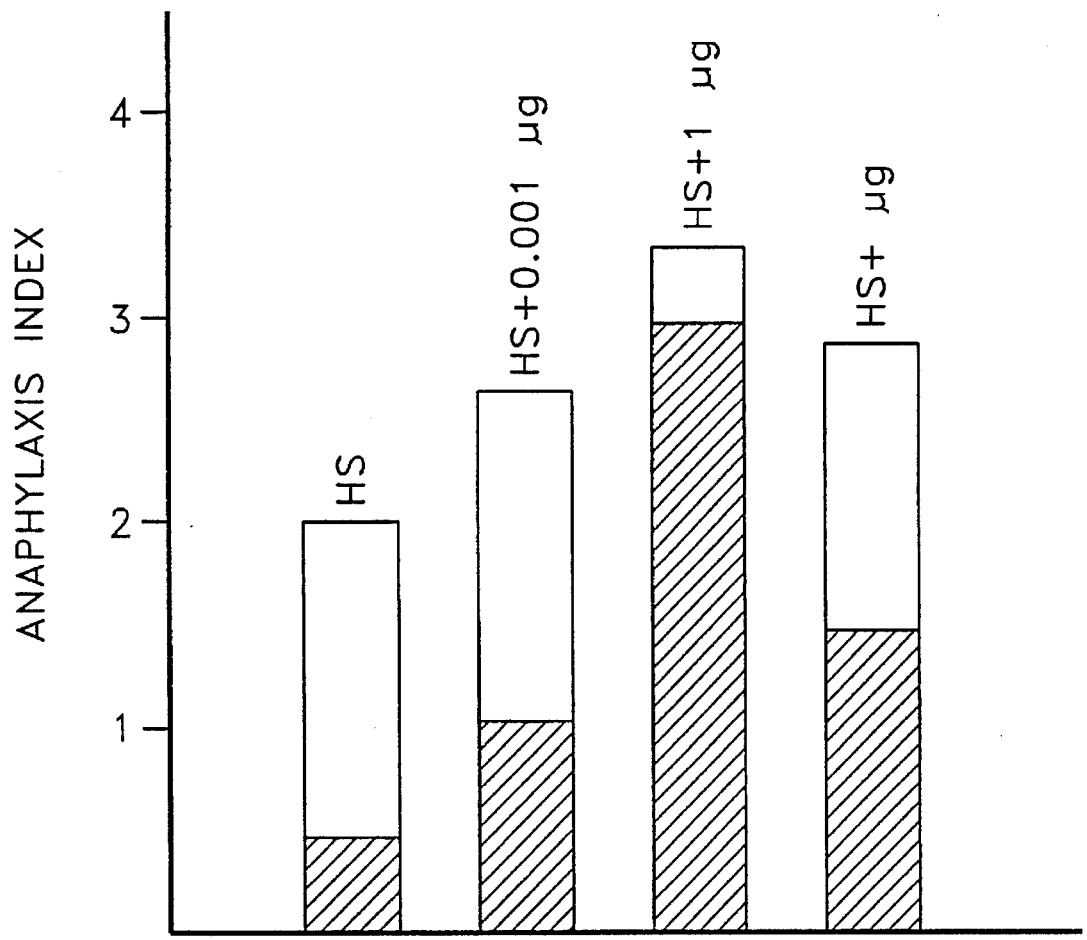
FIG. 2 represents the influence of Synpol-100 on anaphalactic response to horse serum challenge.

The study of specific (immunomodulating) activity revealed the strong stimulating effect of SYNPOL on humoral immune response to sheep red blood cells. The effect was seen within a wide dose range with the optimal dose being 1 μg/mouse (50 μg/kg) (FIG. 1). The stimulation degree was found equal among the high- and low-responder strains of mice but the former ones needed 10-fold less dose of the preparation to reach the same immunostimulation level. Optimal doses of SYNPOL enhanced immediate type reactions antibody-mediated to protein antigen (FIG. 2).

Stimulation of humoral immune response did not result from polyclonal activation of B-cells.

Figure 3:
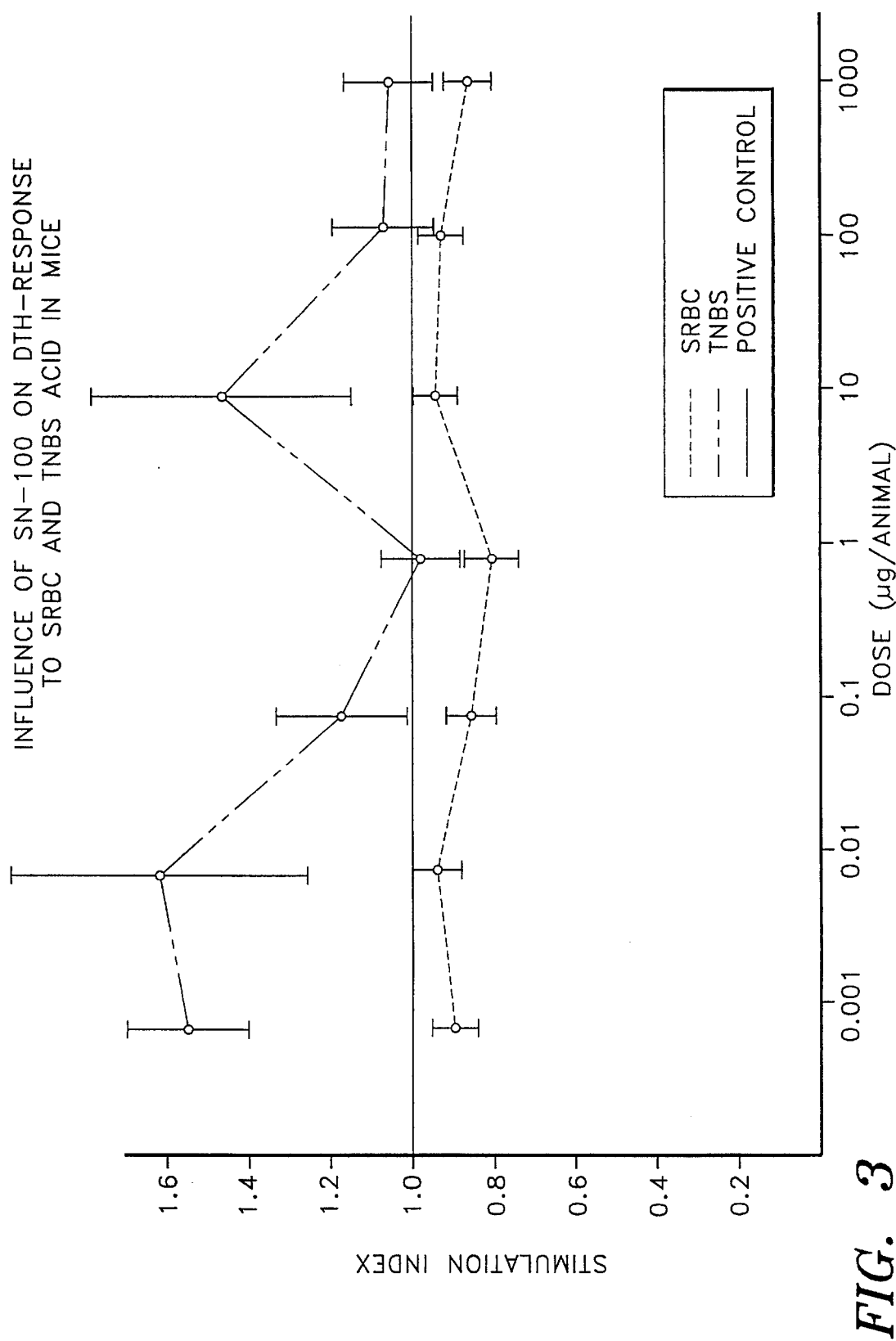
FIG. 3 represents the influence of Synpol-100 on DTH-response to sheep red blood cells and TNBS acid in mice.

Influence of SYNPOL on cell-mediated immunity was diverse and depended both on antigen nature and on the used test system. SYNPOL intensified the delayed type hypersensitivity (DTH) response to TNBS acid but exerted no effect on DTH reaction to sheep red blood cells (FIG. 3) and suppressed graft-versus-host reaction (Table 5).

When studied mechanisms of immunostimulating action, it was revealed that SYNPOL had mitogenic activity on lymphocytes in vitro and in vivo (Table 6), did not manifest mitostatic action, enhanced cooperation of T- and B-cells (Table 7), and exerted no influence on functions and formation of T-suppressors (Tables 8, 9).

Figure 4A:
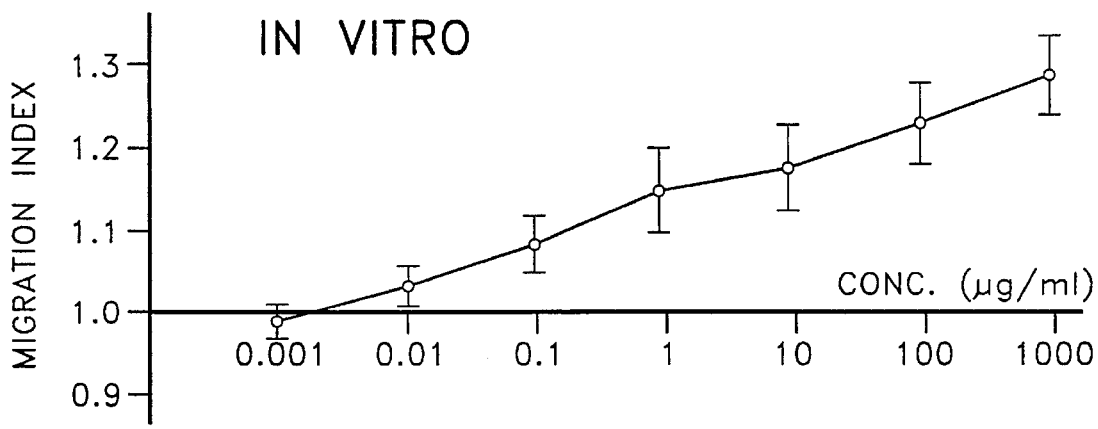
FIGS. 4A and 4B represent the influence of Synpol-100 on spontaneous macrophage migration.
Figure 4B:
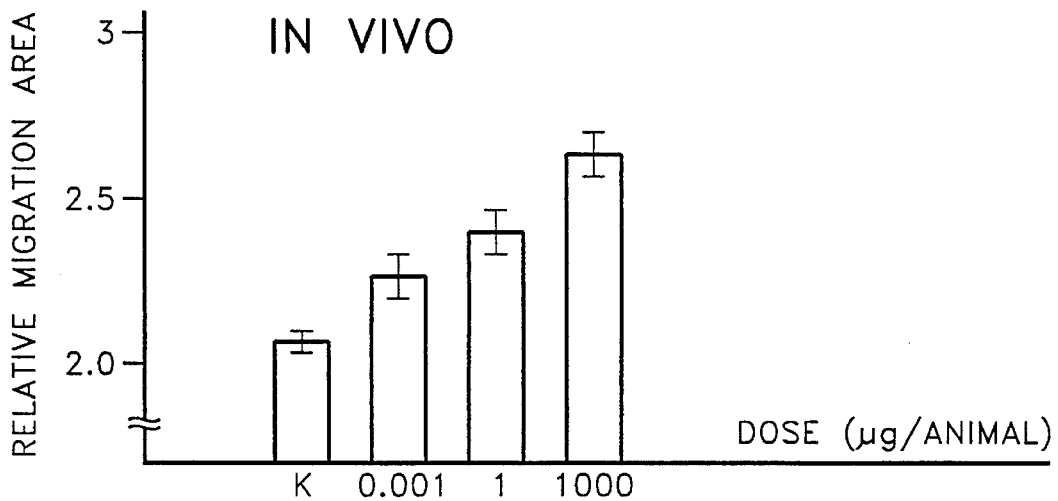
Figure 5:
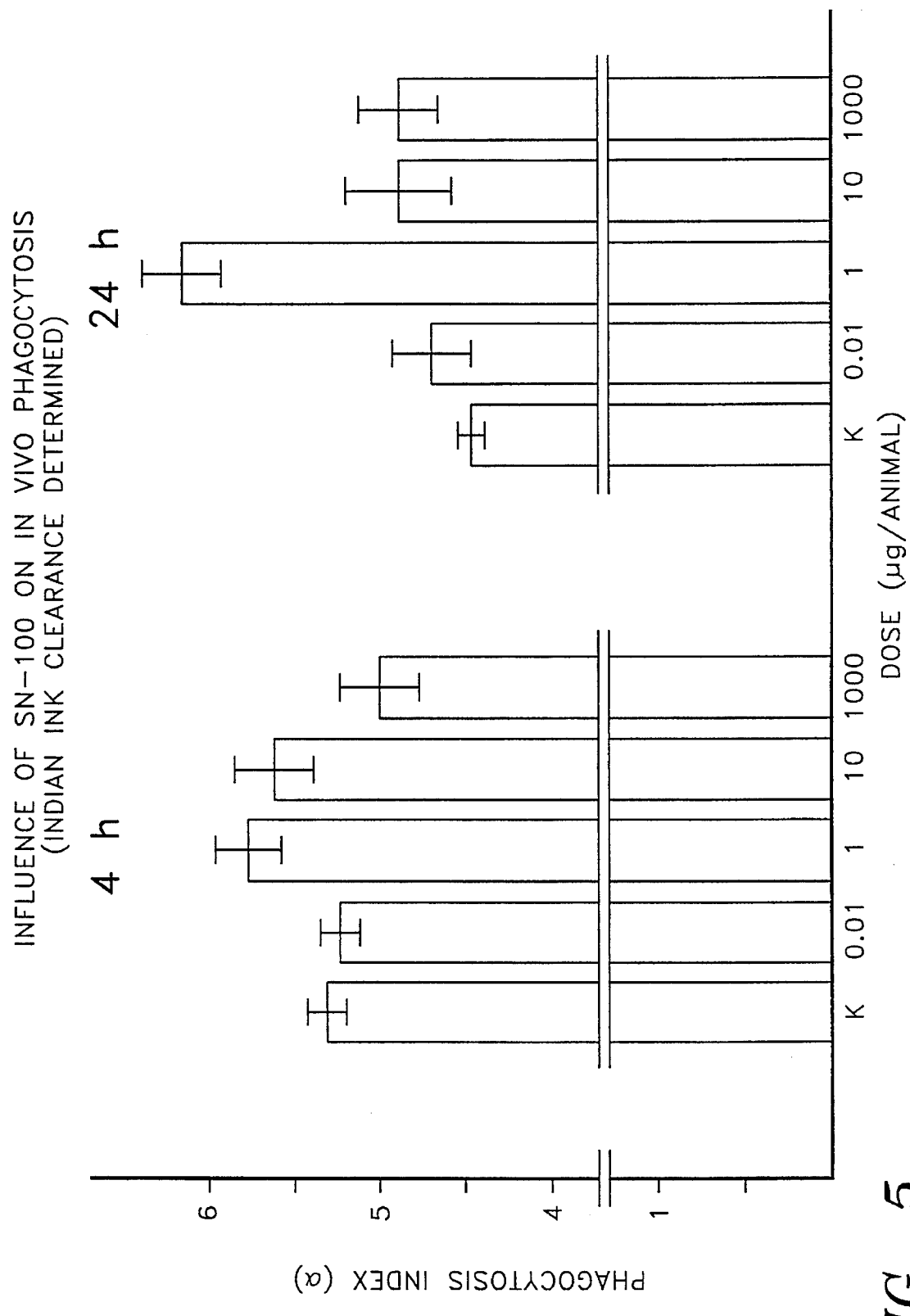
FIG. 5 represents the influence of Synpol-100 on in vivo phagocytosis.
Figure 6:
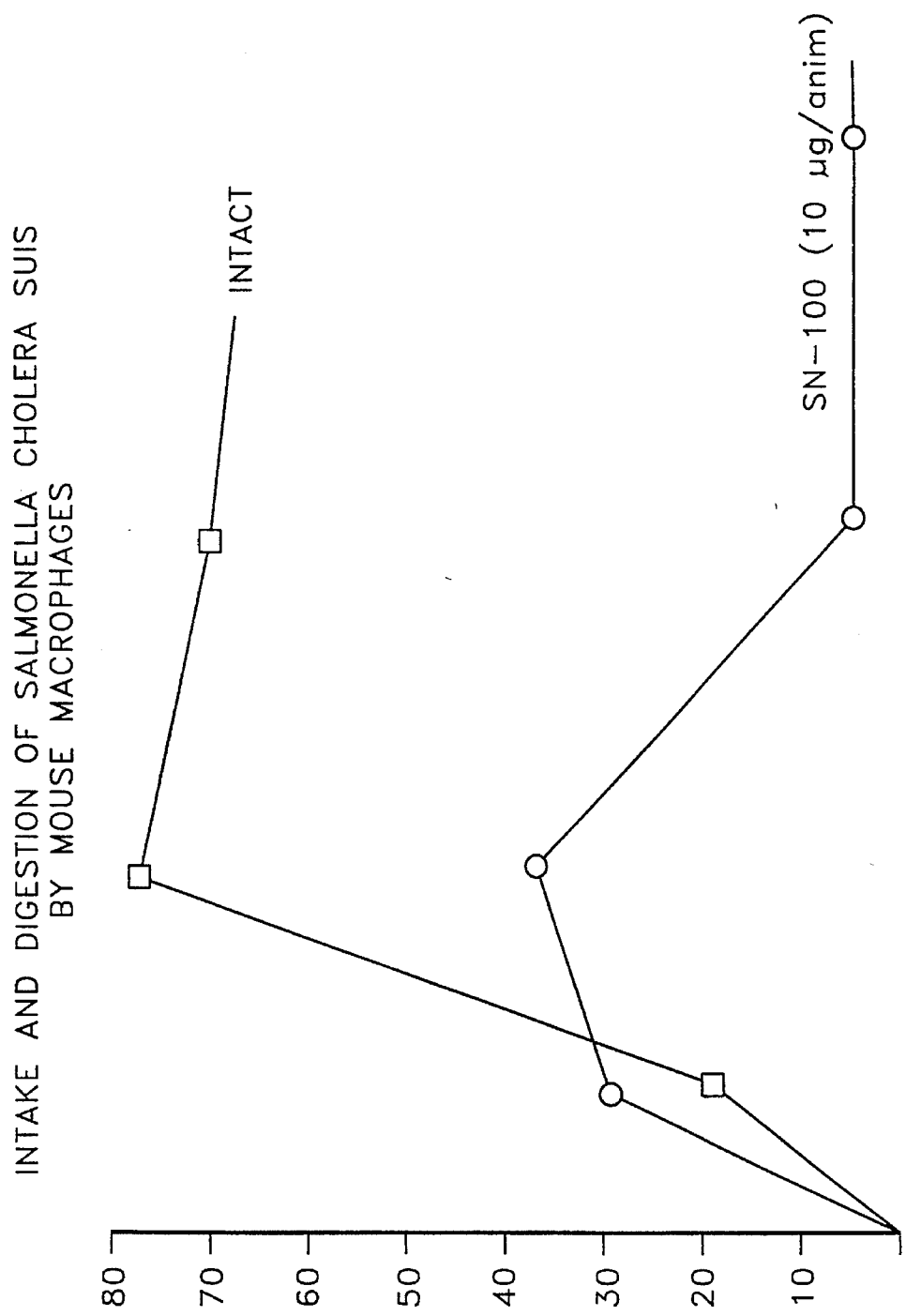
FIG. 6 represents the intake and digestion of *salmonella cholera suis* by mouse macrophages.

The stimulation of macrophages was shown to be one of the important mechanisms of the SYNPOL activity, the polymer intensified macrophage migration (FIG. 4), increased macrophage phagocytic activity in vitro and in vivo, and also enhanced their digesting properties of pathogenic microorganisms (FIGS. 5, 6). SYNPOL's ability to stimulate humoral immune response and phagocyte activity were the reasons for investigation of its immunocorrecting, adjuvant properties at vaccination and protective properties at infection with bacterial strains.

EXAMPLE 10

Pharmacological Activity

The use of Synpot in immunodeficient mice models (CBA, 18 months aged, thymectomized mice, Nu/Nu mice) resulted in normalization of humoral immune response (Table 10).

When influence of SYNPOL on infections was studied its protective effects were found: the preparation, administered 96, 72, 48 or 24 hours before infection with *Salmonella typhimurium* or *Streptococcus pneumoniae* lethal doses prevented the death of the animals (Table 11).

SYNPOL adjuvant properties were studied using both complexes and conjugates with influenza vital surface antigens.

The complex of SYNPOL with haemagglutinin injected increased the HA antibody levels, thus allowing a decreased vaccination dose of the virus (Table 12).

Haemagglutinin-SYNPOL conjugate resulted in more significant immunogenicity of the preparation. Single conjugate injection did not cause intensive antibody production in mice, but provided HA immune memory formation (Tables 13, 14). Twofold conjugate administration resulted in rapid antibody production, and the antibody level was either equivalent or more than the antibody response to significantly higher doses of intact virion influenza vaccine. The formation of long lasting immune memory, IgG antibody production meaning the involvement of T-lymphocytes in the immune reaction are advantages of SYNPOL-based polymer-subunit vaccines.

The SYNPOL antitumor activity has been shown on the following models: Lewis lung epidermal carcinoma (Table 15), pleural mesothelioma (Table 16) and spontaneous carcinogenesis in AKR mice (Table 17).

Antitoxic activity of SYNPOL was studied on $SiO_2$-induced haemolysis of erythrocytes (Table 18) and in mice treated with toxic doses of preparation "MPM". The results indicated SYNPOL protected both the cells and organisms from toxic action.

Pharmacokinetic characteristics estimated SYNPOL to be mainly excreted by the kidneys, 30% during the first day. Half-excretion period is 1.5 h ($t_{1/2}$) for rapid phase and 84 h ($t_{1/2}$) for slow phase. The accumulation level of polymer and its destruction products in tissues was found to be low.

EXAMPLE 11

Chronic Toxicity

A study of general toxicity and specific types of toxicity of SYNPOL was carried out.

The choice of the SYNPOL doses and administration schedule was based on the optimal immunostimulation dose (50 μg/kg) and the SYNPOL content per vaccine dose, recommended for humans. We also took into consideration the possibility of Synpot usage with more frequent administration in patient maximal dose (0.25 mg/kg).

Figure 7:
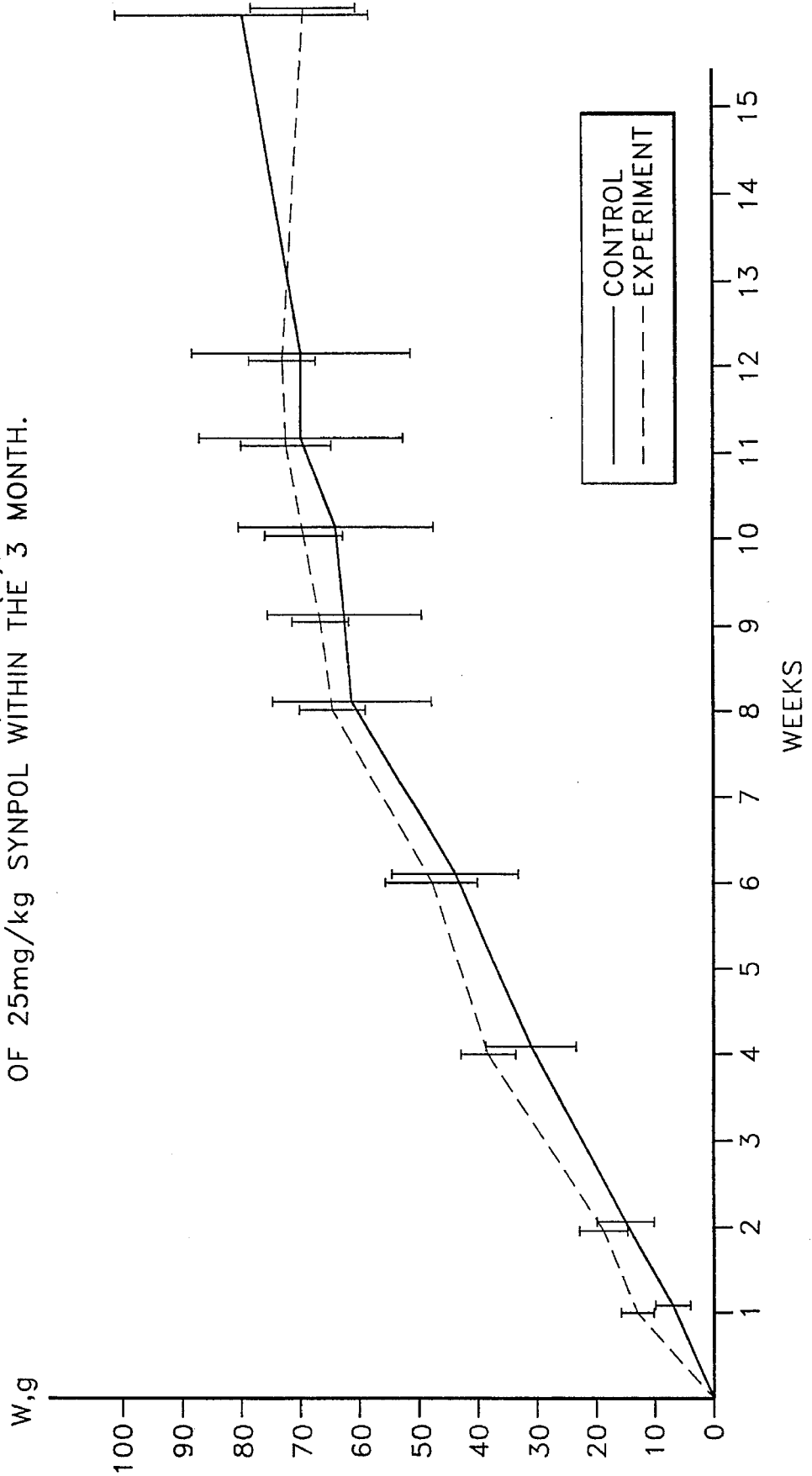
FIG. 7 represents the increase in body mass in rats following injections with SYNPOL.
Figure 8A:
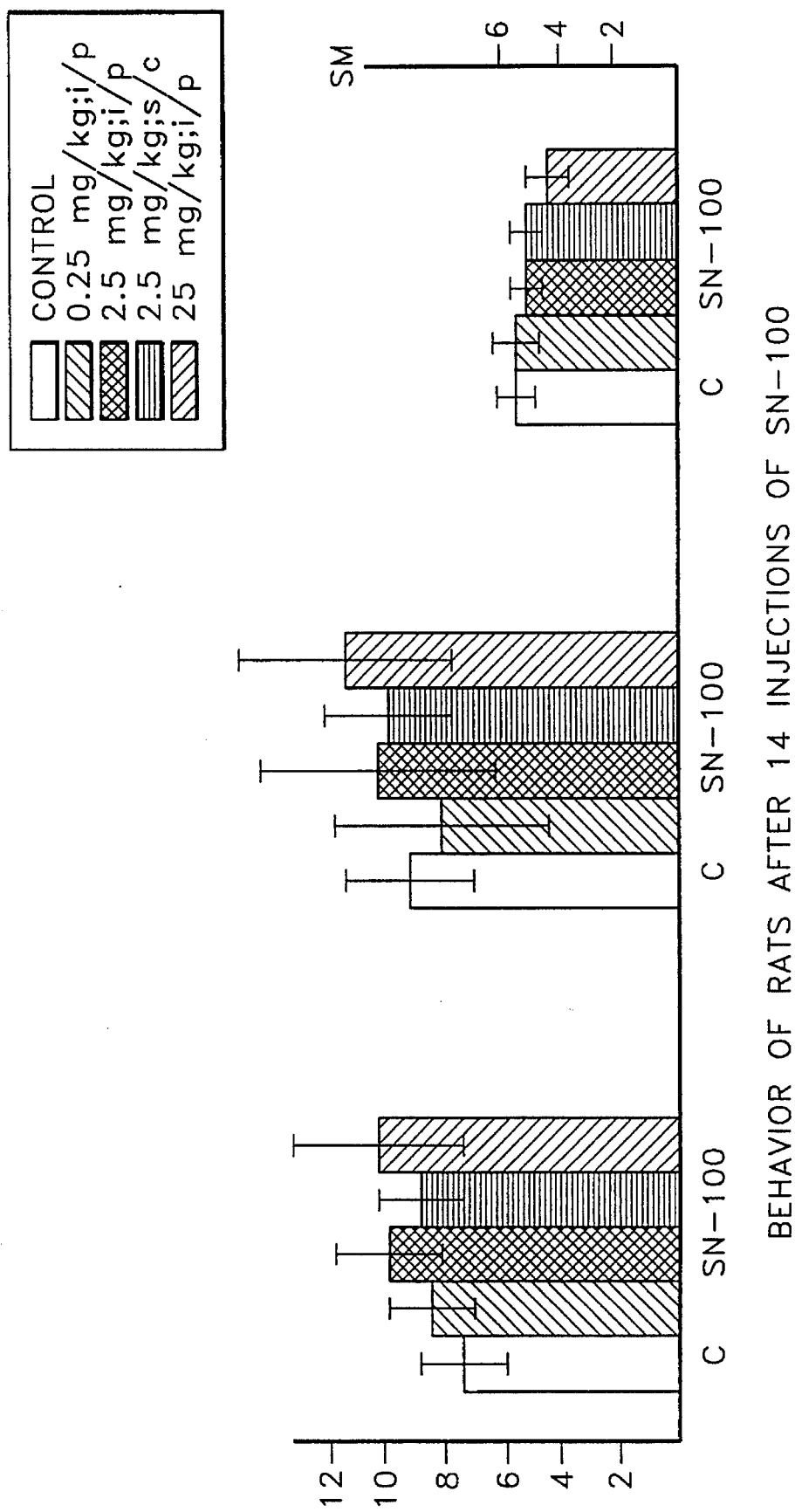
FIG. 8 shows the behavior of rats after 14 injections of Synpol-100.
Figure 8B:
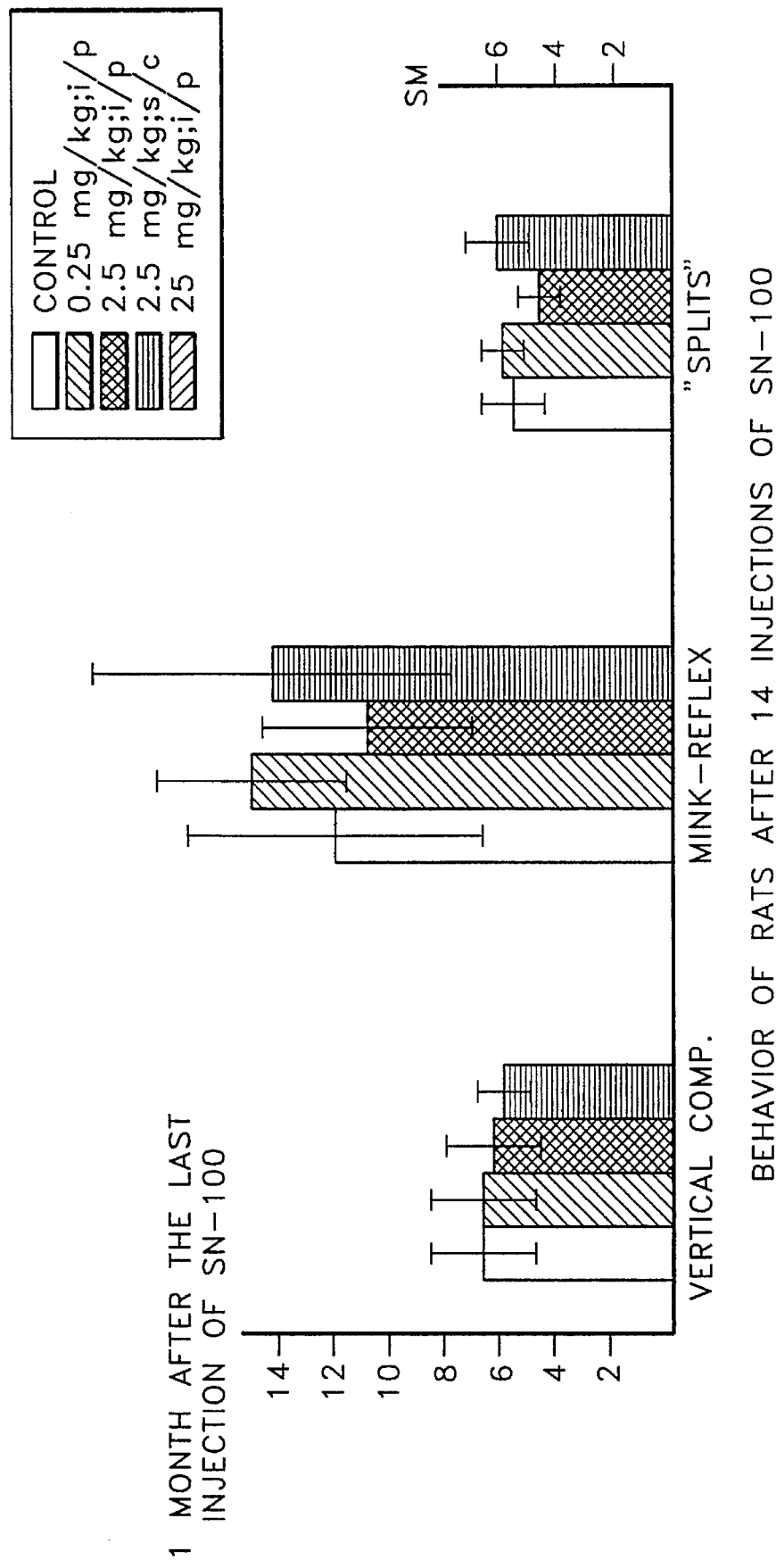

In accordance with the above mentioned conditions of SYNPOL usage the chronic toxicity was studied in two schemes: daily administration to rats and rabbits during two weeks and weekly administration during 3 months to rats and 1 year to AKR mice. We used 0.25, 2.5 and 25 mg/kg doses. These doses are maximal patient dose, 10-fold excess and 100-fold excess maximal patient doses correspondingly. The results of the chronic toxicity study are shown in FIGS. 7–8 and Tables 20–25).

The maximal therapeutic dose recommended for a patient (0.25 mg/kg), administrated daily during 14 days, caused body weight augmentation in comparison to control (29% in males and 52% in females). There were no abnormalities in liver (Table 20–21), kidney (Tables 22–23), central nervous system (FIG. 8) and cardiovascular system functions (Table 24). We noticed an increase in diuresis in females and a leucocyte increase in both males and females (Table 25). The leucocyte rise is likely to be specific activity manifestation. In 14 days after the last injection all the functions were normalized.

A 10-fold dose (2.5 mg/kg) administrated daily during 14 days, caused a delay in body weight increase, a hemoglobin increase and a urine clearance decrease which was recovered from in two weeks. There were no changes in liver, central nervous sytem and cardiovascular system functions. We noted signs of thymus and spleen atrophy and lymph node B-zone activation by histological examination. 10-fold dose (2.5 mg/kg) was used for the study of SYNPOL influence on spontaneous carcinogenesis in AKR mice. This dose treatment during a year did not cause any unfavorable symptoms or changes in animals as compared to control animals.

A 100-fold dose (25 mg/kg) injected daily during 14 days resulted in:

central nervous system function—the increase in the activity of orientation reflexes;

kidney function—urea clearance decrease, kidney glomerular proliferation, kidney function was restored in 2 weeks after the last injection;

peripheral blood—increase of haemoglobin concentration per erythrocyte and its normalization in 2 weeks after the last administration;

lymphoid organs—signs of atrophy in thymus and spleen and lymph node B-zone activation;

cardiovascular system and liver—there were no changes.

No morphological and functional changes were revealed in endocrine organs under all doses and schedules tested.

A 100-fold dose once a week during 3 months caused some body weight increase, muscle tonus rise, an increase of heart pulse rate and an increase in haemoglobin concentration per erythrocyte. No changes were seen in the liver, kidney, and endocrine systems by biochemical and histological methods.

SYNPOL had no allergenic and irritant effects, no mutagenic and teratogenic activities were revealed and a pyrogenic effect was not found. A carcinogenic activity study was finished in 1991. The therapeutic index range of SYNPOL is 400.

The Pharmacological Committee of the USSR Ministry of Public Health Vaccines and Sera Committee of USSR Ministry of Public Health allowed the trials of anti-influenza polymersubunit vaccine (CPS-vaccine) containing SYNPOL as immunostimulator.

During the clinical trial wide safety testing of SYNPOL and the vaccine was performed. Special attention was paid to immunological safety and antigen activity together with evaluations of the main functions of the organism (Table 26).

SYNPOL and the vaccine administration was seen to be well tolerated by volunteers, resulting in neither local nor general reactions. Changes of the immune status of healthy individuals were not observed.

TABLE 4

| Tests for Pre-Clinical Examination of Synpol | | |
|---|---|---|
| System or/and organs | Tests | Animals |
| 1. Immune System | | mice |
| 1.1 Humoral immunity | AFC of spleen, immediate allergy, polyclonal activation | (CBA*C57B1/6)F1 - 6940 |
| 1.2 Cellular immunity | DTH, MMI, GVHR, Ts, mitostatic and lymphotoxic activity, RBTL (T-, B-mitogen), mitogenic activity | CBA - 200; C57B1/6 - 200; guinea pigs - 80 |
| 1.3 Macrophage | Spontaneous migration, phagocytosis | |
| 1.4 Complement | Serum complement titer | |
| 1.5 Allergy | Anaphylaxis, induction of DTH, MMT, leucocytolyse | |
| 2. Pharmacokinetics | Distribution of labelled polyoxidonium in organs and tissues | rats; Wister - 60 |
| 3. Acute toxigenicity | Mass of body, food and water consumption, death, histological examination | mice (CBA*C57B1/6)F1 - 60 |
| 4. Skin, mucosa | Local irritating action | mice, guinea pigs, rabbits rats |

TABLE 4-continued

Tests for Pre-Clinical Examination of Synpol

| System or/and organs | Tests | Animals |
| --- | --- | --- |
| 5. Chronic toxigenicity | | rats |
| 5.1 Integral data | Increase of body mass, outward appearance, intoxication symptom | Wister - 240 |
| 5.2 Liver | Examination of blood serum:glucose, urea, creatinine, total protein, albumins, ALT, AST, total bilirubin, lipoproteide, cholesterin, cholesterin, chloride, calcium, iron | |
| 5.3 Excretion system | Diurnal diuresis, diuresis rate, proteinuria, Glomerular filtration:creatinine clearance excretion of phenolrot. Reabsorbtion:urea clearance, chloride clearance | |
| 5.4 Peripheral blood | Number of erythrocytes, leucocytes, thrombocytes. Differential blood count, Hb, Hct. | |
| 5.5 Heart-ves. system | ECG, pulse, arterial tension | |
| 5.6 Respiration | Frequence of respiration | |
| 5.7 Central and peripheral nervous system | Motor function, orientated reactions, CRPE, algesia, coordinated movement | |
| 5.8 Histological examination of inner organs | | |
| 6. Mutagenicity | Chromosome aberration of bone marrow cells. Dominant lethality of germ cells by mice | mice (CBA*C57B1/6)Fl - 520 |
| 7. Embryotoxigenicity and teratogenicity | | rats; Wister - 150 |

TABLE 5

Influence of SN-100 on Graft vs. Host Reaction

| Dose (μg/mouse) | Number of endogenous colonies in recipient spleen on transplantation of allogenous lymphocytes on doses: | | |
| --- | --- | --- | --- |
| | — | $5 \times 10^5$ | $10^6$ |
| — | 11.5 + 3.9 | 3.0 + 1.6 | 0 |
| 0.001 | | 9.0 + 2.07 | 5.8 + 1.5 |
| 0.01 | | 10.0 + 1.8 | 5.3 + 3.5 |
| 0.1 | | 11.0 + 3.8 | — |
| 1 | | 9.0 + 3.9 | 6.0 + 1.3 |
| 10 | | 11.0 + 4.3 | — |
| 100 | | — | 5.4 + 3.2 |
| 1000 | | 9.0 + 1.6 | 5.6 + 3.4 |
| 2000 | | 12.0 + 4.2 | 6.0 + 0.7 |

TABLE 6

Slight Mitogenic Effect of SN on Mouse Splenocytes

| Cell culture | Stimulation index |
| --- | --- |
| Spleen cells (SC) | 1.0 + 0 |
| SC + ConA (1 μg/ml) | 8.21 + 5.62 |
| SC + LPS (10 μg/ml) | 9.45 + 6.34 |
| SC + PO-100 ($10^{-3}$ μg/ml) | 2.65 + 1.52 |
| SC + PO-100 ($10^{-2}$ μg/ml) | 2.10 + 0.75 |

TABLE 7

Absence of Mitostatic Activity of SN

| Dose (μg/mouse) | Number of endogenous colonies/ spleen of irradiated mice |
| --- | --- |
| — | 11.5 + 3.9 |
| 0.001 | 10.7 + 2.1 |
| 0.01 | 9.1 + 1.3 |
| 0.1 | — |
| 1 | 16.3 + 3.1 |
| 10 | 11.2 + 1.8 |
| 100 | 12.2 + 3.1 |

TABLE 7-continued

Absence of Mitostatic Activity of SN

| Dose (µg/mouse) | Number of endogenous colonies/ spleen of irradiated mice |
|---|---|
| 1000 | 14.4 + 3.2 |
| 2000 | 16.5 + 3.8 |

TABLE 8

Influence of SN-100 on T- and B-Lymphocyte Cooperation

| Group of recipients | Dose (µg) | Number of PFC/spleen |
|---|---|---|
| SRBC | — | 20.0 + 7.8 |
| bone marrow (BM) + SRBC | — | 219.6 + 59.4 |
| thymus (T) + SRBC | — | 124.4 + 34.6 |
| BM + T + SRBC | — | 798.3 + 177.9 |
| " | 0.001 | 1117.7 + 231.3 |
| " | 0.01 | 1384.8 + 199.0 |
| " | 0.1 | 2685.4 + 672.5 |
| " | 1 | 2017.5 + 374.6 |
| " | 10 | 1179.6 + 419.3 |
| " | 100 | 1560.7 + 409.3 |
| " | 1000 | 1282.1 + 808.3 |

Note: Cooperation of T- and B-lymphocytes was enhanced by injection of SN in mice as determined by PFC assay.

TABLE 9

Influence of SN-100 on Activity of Suppressor T-cells

| Spleen cell donor group | Recipient | Suppression index |
|---|---|---|
| — | SRBC | 1.13 + 0.06 |
| SRBC | SRBC | 0.23 + 0.02 |
| SRBC + 0.001 µg | SRBC | 0.29 + 0.03 |
| SRBC + 1 µg | SRBC | 0.28 + 0.04 |
| SRBC + 10 µg | SRBC | 0.21 + 0.02 |
| SRBC + 1000 µg | SRBC | 0.24 + 0.02 |
| SRBC | SRBC + 1 µg | 0.22 + 0.02 |

TABLE 10

Immunocorrection of Antibody Response to SRBC in Immunodeficient Mice With SN

| MICE | Age (mo.) | Dose (µg/kg) | PFC/10$^6$ spleen cells | PFC/spleen |
|---|---|---|---|---|
| CBA | 3–4 | — | 97.6 + 2.44 | 18240 + 544.18 |
| CBA | 16 | — | 12.3 + 0.35 | 1360 + 29.92 |
| CBA | 16 | 10 | 15.6 + 0.51 | 1900 + 45.60 |
| CBA | 16 | 50 | 64.5 + 2.32* | 5130 + 128.25* |
| Nu/Nu | 1.5 | — | 20.0 + 0.72 | 1625 + 47.58 |
| Nu/Nu | 1.5 | 50 | 108.5 + 4.80* | 15520 + 389.05* |
| CBA, B-mice | 5 | — | 22.8 + 0.49 | 1760 + 39.77 |
| CBA, B-mice | 5 | 50 | 160.0 + 3.48* | 12210 + 301.34* |

Injected SN greatly enhanced antibody production in immunodeficient mice.

TABLE 11

Antibacterial Activity of Synpol

| agent (µg/mouse) | Dose of PO (mg/kg) | No. of mice | treatment condition | %% of death |
|---|---|---|---|---|
| *Salmonella typhimurium* T-3.10$^3$ µg | — | 10 | 48 h. before infection, s/c | 100 |
| | 5.0 | 10 | | 38 |
| | 12.5 | 10 | | 50 |
| | 25.0 | 10 | | 75 |
| *Streptococus pneumoniae* 415, 5 × 10$^5$ µg | — | 50 | before infection: | 92 |
| | 0.05 | 40 | 96 h., i/p | 7.8 |
| | 0.5 | 30 | " | 0 |
| | 0.05 | 30 | 72 h., i/p | 8.6 |
| | 5.0 | 30 | " | 29 |
| | 0.5 | 30 | 48 h., i/p | 23 |
| | 50.0 | 30 | " | 93 |
| | 25.0 | 20 | 96 h., s/c | 25 |

Survival raise by SN-treatment 4–2 days before infection.

TABLE 12

Serum Antibody Response in Mice After Two-fold Immunization with Influenza Vaccines (Haemag-glutination Inhibition Determined)

| Antigen | Virus Strain | HA dose (µg/mouse) | PO Dose (mg/kg) | HI titer |
|---|---|---|---|---|
| reference | B/Harkow | 1 | — | 160 |
| | | 0.1 | — | 40 |
| HA | " | 1 | — | 40 |
| | | 0.1 | — | 40 |
| HA + SN | " | 1 | 0.5 | 320 |
| | | 1 | 5.0 | 320 |
| reference | H/Sychuvan | 5.0 | — | 20–40 |
| HA | " | 5.0 | — | 10 |
| CPV | " | 5.0 | 1.0 | 80 |

HA — Haemagglutinin; SN — Synpol; CPV — HA conjugated with SN

TABLE 13

Antiviral Activity of Serum Antibodies

| Immunization | | Immune Response | | | | |
|---|---|---|---|---|---|---|
| B/Leningrad | Dose | primary | | second | | VN |
| 179/86 | (µg) | EIA | HAI | EIA | HAI | test |
| — | — | 500 | 5 | 2,000 | 5 | 10 |
| Reference | 7.5 + 7.5 | 60,000 | 20 | 200,000 | 40 | 400 |
| CPS-V | 1.0 + 1.0 | 10,000 | 20 | 500,000 | 40 | 400 |
| CPS-V | 0.1 + 0.1 | 8,000 | — | 500,000 | 40 | 400 |
| CPS-V | 0.01 + 0.01 | 320 | 5 | 200,000 | 40 | 400 |

TABLE 14

Antibody Isotypes After Booster Injection
Polymer-Conjugated Influenza Vaccine (CPS-V)

| Immunization | Serum anti-HA Antibodies level (as EIA tested) | | | | | |
|---|---|---|---|---|---|---|
| (2*) | IgM | IgA | IgG1 | IgG2$_a$ | IgG2$_b$ | IgG3 |
| 0.01 µg | 3,200 | 800 | 100,000 | 3,200 | 25,600 | 3,200 |
| 0.10 µg | 6,400 | 12,800 | 200,000 | 12,800 | 25,600 | 25,600 |
| 1.00 µg | 12,800 | 50,000 | 200,000 | 200,000 | 200,000 | 100,000 |
| — | 200 | 50 | 50 | 50 | 50 | 50 |

TABLE 15

Influence of SN on Growth of Lewis Carcinoma in C57B1/6 Mice

| Dose (mg/kg) | Observation period (days) | Dead (%%) | Tumor volume (mm) | Tumor %% | Tumor weight (g) | %% |
|---|---|---|---|---|---|---|
| control | 14 | 30 | 6080.25 | 100 | 3.23 | 100 |
| SN, 2.5 (mg/kg) | 14 | 10 | 3679.50 ($p < 0.05$) | 60.6 | 2.18 ($p < 0.05$) | 67.5 |

Note: SN or solvent (control group) injected subcutaneously.

TABLE 16

Effect of SN on Growth of Transplanted Pleural Mesothelium in Rats

| Dose (mg/kg) | Tumor yield (%%) | Mean lifespan (days) | Tumor size (%%) days after challenge | | | | | | |
|---|---|---|---|---|---|---|---|---|---|
| | | | 9 | 13 | 18 | 23 | 26 | 30 | 33 |
| Saline | 80 | 29.3 | 100 | 100 | 100 | 100 | 100 | 100 | 100 |
| SN, 25 mg/kg | 60 | 33.5 | 22.2* | 50.0* | 54.5* | 72.9 | 82.5 | 58.8* | 57.1* |
| SN, 5 mg/kg | 46.7* | 42.4 | 50.0 | 55.4 | 51.0* | 55.0* | 50.1* | 41.1* | 40.3* |

*$p < 0.05$
Note:
25 female rats per group. SN was injected s/c beginning 48 hours after tumor passage followed once (25 mg/kg) or twice (5 mg/kg) a week.

TABLE 17

Effect of SN on Spontaneous Carcinogenesis in AKR mice

| Group | Sex | No. of animals | Tumor yield mice | %% |
|---|---|---|---|---|
| Control | females | 21 | 18 | 85.7 + 7.6 |
| | males | 21 | 14 | 66.7 + 10.3 |
| | females | 19 | 14 | 73.6 + 10.3 |
| | males | 18 | 5 | 27.8 + 10.5 |

Note:
SN was injected subcutaneously once a week at 2.5 mg/kg dose during 40 weeks.

TABLE 18

Protective Effect of Polymers on SiO$_2$-Induced (DQ-12, 3 mg/ml) Haemolysis of Human Red Blood Cells

| Substance Tested | | | Protection |
|---|---|---|---|
| Name | Mm (Kd) | Conc. (mg/ml) | (%) |
| Synpol | 20 | 1 | 35 |
| | | 5 | 75 |
| | | 10 | 98 |
| | | 50 | 100 |
| | 120 | 1 | 37 |
| | | 5 | 73 |
| | | 10 | 92 |
| | | 50 | 100 |
| Polyvinylpyridine-N-oxide | 100 | 50 | 87 |
| | | 100 | 100 |
| Polyvinylpyrrolidone (PVP) | 80 | 250 | 52 |
| | | 1000 | 83 |

TABLE 19

Protective Effect of Synpol on Acute Toxicity of MPM in Mice at Intraperitoneal Injection

| Group | Dose | quantity of mice | alive/dead |
|---|---|---|---|
| Saline | 0.5 ml | 6 | 0/6 |
| MPM | 5 mg/kg | 6 | 3/3 |
| MPM | 10 mg/kg | 6 | 6/0 |
| MPM + SN | 10 + 50 mg/kg | 6 | 1/5 |

Note:
Mice died between 2 and 5 days after injection of MPM. Time of observation 21 days.

TABLE 20

Blood serum biochemical dates, rats ($\male$) after 14 injections of Synpol (series 1)

| DATE | unit | CONTROL | EXPERIMENT | | | |
|---|---|---|---|---|---|---|
| | | | 0.25 mg/kg | 2.5 mg/kg | 2.5 mg/kg (s/c) | 25 mg/kg |
| Mass coeff of liver | | 3.71 + 0.12 | 3.85 + 0.17 | 3.63 + 0.11 | 3.52 + 0.12 | 4.02 + 0.16 |
| Glucose B | mM/l | 7.52 + 0.20 | 7.09 + 0.19 | 8.34 + 0.79 | 69.3 + 0.47 | 8.35 + 0.25* |
| Urea | mM/l | 3.49 + 0.17 | 3.77 + 0.28 | 4.37 + 0.08* | 4.71 + 0.25* | 4.60 + 0.29* |
| Creatinine | μM/l | 45.3 + 1.9 | 50.4 + 2.3 | 46.9 + 3.2 | 51.5 + 2.6 | 47.1 + 4.2 |
| Total bilirub. | μM/l | 1.40 + 0.09 | 1.70 + 0.12 | 1.20 + 0.12 | 1.20 + 0.13 | 1.30 + 0.35 |
| Total protein | g/l | 72.0 + 1.29 | 69.5 + 1.04 | 70.5 + 1.15 | 74.4 + 1.61 | 68.9 + 1.20 |
| Albumin | g/l | 34.8 + 0.79 | 33.3 + 1.07 | 34.1 + 0.72 | 36.7 + 1.23 | 37.6 + 1.09 |
| Haptoglobin | g/l | 0.31 + 0.25 | — | 0.31 + 0.06 | 0.28 + 0.04 | 0.28 + 0.06 |
| Celluroplasma | U/l | 382.0 + 66.3 | — | 315.0 + 29.8 | 316.0 + 30.6 | 281.0 + 36.1 |
| A L T | U/l | 76.2 + 3.99 | 86.3 + 5.60 | 64.7 + 4.76 | 72.9 + 8.80 | 78.5 + 6.31 |
| A S T | U/l | 333.5 + 13.2 | 364.0 + 12.8 | 359.9 + 12.9 | 364.0 + 15.3 | 352.7 + 17.1 |
| Alc. phosph. | U/l | 110.1 + 10.1 | 115.5 + 7.9 | 80.5 + 3.45 | 98.2 + 8.6 | 114.7 + 6.8 |
| -amylase | kU/l | 13.9 + 0.22 | 14.1 + 0.12 | 14.0 + 0.40 | 14.0 + 0.18 | 14.5 + 0.22 |
| $Ca^{2+}$ | mM/l | 2.50 + 0.01 | 2.49 + 0.02 | 2.42 + 0.04 | 2.38 + 0.05 | 2.53 + 0.03 |
| $Fe^{3+}$ | μM/l | 63.7 + 4.4 | — | 64.9 + 2.4 | 61.8 + 5.8 | 42.1 + 9.7 |
| $Cl^-$ | mM/l | 106.7 + 0.83 | 106.9 + 0.83 | 107.0 + 0.95 | 108.5 + 0.95 | 106.1 + 0.71 |
| -LP | mg/% | 48.6 + 4.64 | 45.5 + 2.90 | 54.0 + 4.70 | 48.3 + 3.73 | 52.0 + 8.40 |

TABLE 21

Blood serum biochemical dates, rats ($\female$) after restore period (series 2)

| DATE | unit | CONTROL | EXPERIMENT | | | |
|---|---|---|---|---|---|---|
| | | | 0.25 mg/kg | 2.5 mg/kg | 2.5 mg/kg (s/c) | 25 mg/kg |
| Glucose B | mM/l | 8.63 + 0.42 | 9.18 + 0.43 | 8.30 + 0.17 | 9.02 + 0.48 | 7.48 + 0.24 |
| Urea | mM/l | 5.62 + 0.39 | 6.40 + 0.53 | 5.51 + 0.35 | 5.38 + 0.22 | 6.89 + 0.65 |
| Creatinine | μM/l | 48.5 + 3.45 | 49.1 + 1.67 | 39.4 + 2.80 | 47.5 + 1.67 | 54.3 + 1.60 |
| Total bilirub. | μM/l | 0.60 + 0.12 | 0.70 + 0.19 | — | 0.60 + 0.14 | — |
| Total protein | g/l | 68.4 + 2.68 | 72.8 + 1.00 | 71.2 + 1.78 | 72.3 + 3.34 | 69.6 + 3.19 |
| Albumin | g/l | 32.4 + 1.56 | 34.8 + 0.97 | 32.7 + 1.13 | 35.8 + 1.69 | 31.2 + 2.05 |
| A L T | U/l | 68.1 + 6.15 | 73.1 + 5.20 | 68.0 + 7.00 | 69.9 + 5.95 | 76.0 + 18.9 |
| A S T | U/l | 51.3 + 6.75 | 61.0 + 5.46 | 58.0 + 12.2 | 58.7 + 7.14 | 61.3 + 15.1 |
| α-amylase | kU/l | 13.1 + 0.12 | 12.8 + 0.17 | 13.9 + 0.12 | 12.6 + 0.46 | 13.3 + 0.43 |
| $Ca^{2+}$ | mM/l | 2.51 + 0.04 | 2.43 + 0.05 | 2.49 + 0.05 | 2.44 + 0.03 | 2.45 + 0.05 |
| $Fe^{3+}$ | μM/l | 48.8 + 4.09 | 56.6 + 4.17 | 59.3 + 8.70 | 51.1 + 2.96 | — |
| $Cl^-$ | mM/l | 114.0 + 2.38 | 113.0 + 1.19 | 112.0 + 1.19 | 112.0 + 2.14 | 108.0 + 2.83 |
| -LP | mg/% | 37.8 + 3.33 | 40.0 + 4.43 | 43.4 + 4.39 | 37.5 + 4.27 | 45.4 + 4.53 |

TABLE 22

Examination of kidney function by rats (♀) after 14 injections of Synpol (Series 2)

| Tests | Control | 0.25 mg/kg | 2.5 mg/kg | 2.5 mg/kg (s/c) | 25 mg/kg |
|---|---|---|---|---|---|
| Masscoefficient | 0.66 + 0.01 | 0.71 + 0.019* | 0.71 + 0.017* | 0.71 + 0.023 | 0.70 + 0.020 |
| Diurnaldiuresis (ml) | 9.11 + 0.61 | 9.75 + 0.69 | 9.45 + 1.11 | 9.38 + 0.66 | 9.49 + 0.32 |
| PROTEIN: | | | | | |
| serumal, g/l | 72.0 + 1.29 | 69.5 + 1.04 | 70.5 + 1.15 | 74.4 + 1.61 | 68.9 + 1.20 |
| urinary, g/l | 4.19 + 0.25 | 3.81 + 0.39 | 4.08 + 0.22 | 3.52 + 0.25 | 3.56 + 0.24 |
| urinary, g/day × $10^{-3}$ | 37.4 + 3.1 | 38.2 + 4.9 | 38.7 + 4.6 | 33.0 + 3.3 | 33.4 + 2.53 |
| CREATININE: | | | | | |
| serumal, μM/l | 45.3 + 1.94 | 50.4 + 2.26 | 46.9 + 3.21 | 51.5 + 2.6 | 47.1 + 4.17 |
| urinary, μM/l | 7112 + 1107 | 6471 + 460 | 7472 + 790 | 7323 + 598 | 6205 + 463 |
| urinary, μM day | 68.0 + 7.8 | 62.3 + 5.4 | 59.0 + 7.4 | 62.3 + 4.6 | 58.2 + 3.2 |
| clearance, ml/min | 1.01 + 0.07 | 0.86 + 0.06 | 1.02 + 0.12 | 0.94 + 0.12 | 0.91 + 0.12 |
| UREA: | | | | | |
| serumal, mM/l | 3.49 + 0.17 | 3.77 + 0.28 | 4.37 + 0.08* | 4.71 + 0.25* | 4.60 + 0.29 |
| urinary, mM/l | 538.6 + 83.3 | 508.5 + 58.3 | 552.8 + 65.5 | 575.7 + 44.6 | 535.9 + 49.5 |
| urinary, mM/day | 4.8 + 0.6 | 4.9 + 0.6 | 5.07 + 0.8 | 4.9 + 0.57 | 4.96 + 0.36 |
| clearance, ml/min | 0.97 + 0.14 | 0.88 + 0.10 | 0.88 + 0.13 | 0.76 + 0.09 | 0.77 + 0.11 |
| excret. fraction, % | 93.8 + 8.4 | 103.1 + 10.6 | 78.6 + 9.6 | 85.0 + 11.9 | 87.4 + 16.2 |
| CHLORIDE: | | | | | |
| serumal, mM/l | 106.7 + 0.83 | 106.9 + 0.83 | 107.0 + 0.95 | 108.5 + 0.95 | 106.1 + 0.71 |
| urinary, mM/l | 68.0 + 5.3 | 62.5 + 9.6 | 54.6 + 6.0 | 64.2 + 4.68 | 56.4 + 5.4 |
| urinary, mM/day | 0.58 + 5.3 | 0.61 + 0.10 | 0.52 + 0.08 | 0.58 + 0.06 | 0.54 + 0.05 |
| clearance, ml/min × $10^{-3}$ | 3.79 + 0.30 | 3.96 + 0.49 | 3.41 + 0.39 | 3.71 + 0.38 | 4.52 + 0.36 |
| excret. fraction, % | 0.39 + 0.03 | 0.46 + 0.07 | 0.34 + 0.07 | 0.40 + 0.04 | 0.41 + 0.048 |

TABLE 23

Examination of kidney function by rats (♀) at the end of restore period after injection of Synpol (Series 2)

| Tests | Control | 0.25 mg/kg | 2.5 mg/kg | 2.5 mg/kg (s/c) | 25 mg/kg |
|---|---|---|---|---|---|
| Masscoefficient | 0.64 + 0.013 | 0.64 + 0.015 | 0.66 + 0.021 | 0.66 + 0.020 | 0.63 + 0.013 |
| Diurinaldiuresis (ml) | 10.7 + 0.56 | 10.2 + 0.66 | 12.0 + 1.09 | 11.3 + 0.79 | 8.5 + 0.85* |
| PROTEIN: | | | | | |
| serumal, g/l | 68.4 + 2.68 | 72.8 + 1.00 | 72.1 + 1.78 | 72.3 + 3.34 | 69.6 + 3.19 |
| urinary, g/l | 5.94 + 0.56 | 6.20 + 0.51 | 4.81 + 0.18 | 5.36 + 0.28 | 6.90 + 0.85 |
| urinary, g/day | 0.06 + 0.005 | 0.06 + 0.004 | 0.06 + 0.007 | 0.06 + 0.006 | 0.05 + 0.006 |
| CREATININE: | | | | | |
| serumal, μM/l | 48.5 + 3.45 | 49.1 + 1.67 | 39.4 + 2.3 | 47.5 + 1.67 | 54.3 + 1.6 |
| urinary, μM/l | 6593 + 391.2 | 7577 + 448.7 | 5803 + 358.3 | 7276 + 642.4 | 8761 + 1284 |
| urinary, μM/day | 67.3 + 3.7 | 76.3 + 4.4 | 68.9 + 6.0 | 80.9 + 6.4 | 62.7 + 5.3 |
| clearance, ml/min | 1.03 + 0.13 | 1.09 + 0.12 | 1.24 + 0.07 | 1.11 + 0.10 | 0.77 + 0.18 |
| UREA: | | | | | |
| serumal, mM/l | 5.62 + 0.39 | 6.40 + 0.53 | 5.51 + 0.35 | 5.38 + 0.22 | 6.89 + 0.65 |
| urinary, mM/l | 547.0 + 61.4 | 547.0 + 67.5 | 479.0 + 23.8 | 590.0 + 51.8 | 658.0 + 119.0 |
| urinary, mM/day | 5.4 + 0.56 | 5.4 + 0.64 | 5.7 + 0.51 | 6.5 + 0.47 | 5.2 + 0.42 |
| clearance, ml/min | 0.85 + 0.16 | 0.64 + 0.04 | 0.76 + 0.10 | 0.85 + 0.08 | 0.49 + 0.18* |
| excret. fraction, % | 90.7 + 15.3 | 60.4 + 3.4 | 59.3 + 10.8 | 69.8 + 10.7 | 66.5 + 25.6 |
| CHLORIDE: | | | | | |
| serumal, mM/l | 114.0 + 2.38 | 113.0 + 1.19 | 112.0 + 1.19 | 112.0 + 2.14 | 108.0 + 2.83 |
| urinary, mM/l | 67.2 + 3.4 | 78.3 + 3.0* | 74.7 + 3.1 | 77.4 + 6.5 | 66.1 + 0.05 |
| urinary, mM/day | 0.69 + 0.07 | 0.80 + 0.07 | 0.89 + 0.08 | 0.85 + 0.06 | 0.54 + 0.05 |
| clearance, ml/min * $10^{-3}$ | 4.20 + 0.41 | 4.90 + 0.42 | 5.50 + 0.49 | 5.21 + 0.38 | 3.78 + 0.57 |
| excret. fraction, % | 0.47 + 0.06 | 0.47 + 0.05 | 0.40 + 0.02 | 0.44 + 0.02 | 0.52 + 0.05 |

TABLE 24

Heart pulse rate in female rats after multiple injection of Synpol

| Dose (mg/kg) and route | n | Background | After 12 injections | 1 mo. after the last injection |
|---|---|---|---|---|
| Daily | | | | |
| Saline, i/p | 8 | 452 + 17.2 | 438 + 14.0 | 438 + 14.0 |
| 0.25, i/p | 7 | 440 + 14.4 | 436 + 22.2 | 452 + 16.2 |
| 2.5, i/p | 9 | 453 + 14.3 | 455 + 10.0 | 449 + 14.2 |
| 2.5, s/c | 9 | 433 + 11.4 | 441 + 15.7 | 442 + 18.5 |
| 25, i/p | 9 | 481 + 11.4 | 477 + 11.4 | — |
| Weekly | | | | |
| Saline, s/c | 10 | 448 + 13.0 | 467 + 9.1 | 492 + 17.6* |
| 25, s/c | 9 | 433 + 10.0 | 482 + 7.1* | 480 + 11.4* |

*Significant difference at $p < 0.05$

TABLE 25

Blood examination by rats (♀) at different times after injection of Synpol

| GROUP | Leukocytes (* $10^6$/l) | Erythrocytes (* $10^{12}$/l) | Hematocrit | Hemoglobin (g/l) | Color index | Hb proerythrocyte |
|---|---|---|---|---|---|---|
| After 14 injections: | | | | | | |
| Control | 15.0 + 1.1 | 4.91 + 0.29 | 0.46 + 0.022 | 120 + 3.0 | 0.75 + 0.04 | 26.7 + 0.8 |
| 0.25; i/p | 20.8 + 1.4 | 5.11 + 0.17 | 0.48 + 0.024 | 117 + 1.0 | 0.70 + 0.02 | 24.9 + 0.9 |
| 2.5; i/p | 17.3 + 1.7 | 5.15 + 0.71 | 0.48 + 0.066 | 122 + 3.0 | 0.72 + 0.02 | 25.4 + 0.7 |
| 25; i/p | 16.4 + 2.1 | 5.07 + 0.10 | 0.48 + 0.095 | 120 + 4.0 | 0.70 + 0.03 | 25.4 + 0.9 |
| 2.5; s/c | 13.1 + 1.0 | 4.45 + 0.29* | 0.42 + 0.03 | 114 + 2.0 | 0.83 + 0.09* | 29.3 + 3.2* |
| 2 weeks after last injection: | | | | | | |
| Control | 10.0 + 0.6 | 4.84 + 0.20 | 0.45 + 0.018 | 121 + 1.0 | 0.76 + 0.03 | 27.1 + 1.1 |
| 0.25; i/p | 14.3 + 1.1 | 4.61 + 0.24 | 0.43 + 0.023 | 113 + 2.0 | 0.75 + 0.04 | 26.5 + 1.4 |
| 2.5; i/p | 11.1 + 1.8 | 4.77 + 0.18 | 0.45 + 0.015 | 112 + 2.6 | 0.70 + 0.02 | 25.0 + 0.7 |
| 25; i/p | 18.3 + 2.0* | 5.04 + 0.34 | 0.47 + 0.043 | 119 + 1.0 | 0.75 + 0.09 | 26.9 + 3.3 |
| 2.5; s/c | 13.2 + 1.2 | 5.46 + 0.16* | 0.51 + 0.014* | 117 + 2.0 | 0.64 + 0.02 | 22.9 + 0.8* |
| 4 weeks after last injection: | | | | | | |
| Control | 15.5 + 2.8 | 5.05 + 0.81 | 0.47 + 0.08 | 107 + 2.0 | 0.64 + 0.01 | 22.8 + 0.4 |
| 0.25; i/p | 16.1 + 1.6 | 4.95 + 0.14 | 0.46 + 0.09 | 114 + 2.0 | 0.70 + 0.01 | 24.7 + 0.5 |
| 2.5; i/p | 15.5 + 0.9 | 4.87 + 0.16 | 0.46 + 0.02 | 106 + 2.0 | 0.66 + 0.04 | 23.6 + 1.4 |
| 25; i/p | 17.6 + 1.8 | 4.71 + 0.64 | 0.44 + 0.06 | 105 + 2.0 | 0.66 + 0.01 | 23.8 + 0.4 |
| 2.5; s/c | 15.2 + 1.4 | 4.97 + 0.14 | 0.46 + 0.03 | 104 + 3.0 | 0.63 + 0.02 | 22.5 + 0.7 |

Note:
*authentic distinctions with background-value

EXAMPLE 12

Immunostimulating Properties of SYNPOL

The immunostimulating activity of SYNPOL was estimated by the number of antibody forming cells generated on the 4th–7th day in the spleen of mice immunized by sheep erythrocytes and also by the protection of chickens—broilers from a number of vital and bacterial infections.

The stimulation coefficient determined by Erne reaction varied depending on SN dose and molecular mass in 3–12 range. The study on the anti-virus activity (Newcastle disease) conducted at the poultry factory on chickens-broilers has demonstrated a considerable reduction of the chicken loss and body mass increase in comparison with the control in aerosol and peroral methods of the preparation injection.

The antibacterial activity of SN was studied in the tests on the determination of mice non-specific resistance to the infection of salmonella streptococcosis and also on chickens-broilers in the concurrent infection (mycoplasmoses, colibacilloses, salmonelloses).

After a single parenteral injection of SN, mice remain for 10–15 days resistant to the infection by a lethal dose of the exciter. Aerosol processing of chickens-broilers by SYNPOL protects them from diseases resulting from the above-listed infections. Daily average weight increases for the chickens treated by SN were 30 g (control-17 g). The preservation was 95 and 60%, respectively. Together with the preservation and productivity of poultry the application of antibiotics is dramatically reduced which provides for ecologically clean poultry products.

TABLE 26

Immune Status Before/After Vaccination with Influenza CPS-Vaccine

| | CPS - vaccine | | | |
|---|---|---|---|---|
| Synpol | before | 21 days after | before | 21 days after |
| Leucocytes (thousands) | 4.5 + 0.5 | 6.2 + 0.3 | 4.7 + 0.7 | 5.7 + 0.5 |
| Lymphocytes (%) | 36.9 + 1.9 | 32.5 + 2.4 | 36.9 + 2.6 | 32.4 + 3.4 |
| Tlymph. | 72.6 + 1.2 | 81.7 + 1.7 | 68.7 + 3.3 | 74.5 + 2.9 |

TABLE 26-continued

Immune Status Before/After Vaccination with Influenza CPS-Vaccine

| Synpol | CPS - vaccine | | | |
|---|---|---|---|---|
| | before | 21 days after | before | 21 days after |
| (E-RFC) (%) | | | | |
| Blymph. | 12.4 + 1.3 | 13.2 + 1.3 | 12.3 + 1.0 | 11.2 + 1.2 |
| (EAC-RFC) (%) | | | | |
| T-helpers (T) (%) | 56.9 + 2.1 | 59.7 + 2.3 | 53.2 + 2.5 | 57.6 + 3.4 |
| T-suppressors (T) (%) | 4.4 + 2.7 | 5.9 + 3.2 | −0.2 + 1.2 | 3.7 + 2.2 |
| Phagocytosis (%) | 52.3 + 2.9 | 55.7 + 4.3 | 41.8 + 3.2 | 56.9 + 5.7 |
| IgA (mg %) | 202.8 + 24.2 | 203.6 + 26.5 | 222.0 + 22.0 | 207.2 + 35.0 |
| IgM (mg %) | 162.7 + 19.5 | 162.5 + 23.9 | 226.0 + 44.0 | 171.0 + 22.0 |
| IgG (mg %) | 1203.0 + 58.8 | 1104.0 + 67.5 | 1394.0 + 110.0 | 1173.0 + 59.0 |
| IgE (total) (kU/l) | 209.6 + 61.5 | 196.8 + 66.4 | 98.9 + 30.0 | 89.0 + 21.0 |
| CIC (unit) | 6.2 + 0.9 | 6.3 + 2.6 | 7.6 + 1.2 | 5.6 + 1.9 |

EXAMPLE 13

Immunoadjuvant Properties of SYNPOL

The combined injection of SYNPOL with protein or peptide antigens leads to the induction of the antibody response to antigen 5–10 times higher than with the injection of antigen itself.

For illustration, Table 27 presents data for PO immunoadjuvant action with the induction of the antibody response to a protein antigen using mice (CBA×C57BL) FI. Antigen was hypodermically injected in optimal immunogenic doses of 2 μg. Various SN doses were injected mixed with antigen. The level of the antibodies specific to antigen was estimated by the immunoferment method. In Table 27 the inverse values for titers of mouse blood serum immunized by antigen or antigen and SN mixture are presented. For comparison, the complete Freund adjuvant (CFA) immunoadjuvant action is presented.

TABLE 27

| | Primary Immune Response | | Secondary Immune Response | |
|---|---|---|---|---|
| Group period | 2nd Week | 4th Week | 2nd Week | 4th Week |
| 1000 mcg SN 2 mcg AG | 2121 (1485–2757) | 4770 (3339–6201) | 8195 (5737–10654) | 24362 (13980–34744) |
| 10 mcg SN 2 mcg AG | 207 (145–269) | 909 (636–1181) | 1564 (1095–2033) | 1958 (1371–2545) |
| Physiological solution 2 mcg AG | 0 | 0 | 240 (168–312) | 1262 (884–1641) |
| CFA 2 mcg AG | 2191 (1534–2848) | 9562 (2310–16814) | 29634 (20744–38524) | 15388 (3374–27401) |

The confidence interval at P=0.05 is indicated in brackets.

From the data given in Table 27 it is seen that SN and antigen mixed introduction leads to the development of a considerable primary response and high secondary antibody I o C response. Besides, the secondary reaction not only does not exceed the level of the response to antigen 10–20 times but it began earlier and took longer.

In Tables 28 and 29 results of SN immunoadjuvant action in mice immunization (CBA×C57BL) FI by synthetic peptides, particularly, by peptide analogues of the antigen determinant of AIDS proteins is presented. It is seen that SN immunoadjuvant action can be rather strong (Table 28) and relatively weak (Table 29). The differences, apparently, are related not to immunostimulating but with the physical—chemical peptides used as antigens (the difference in hydrophilic-hydrophobic balance of peptides).

TABLE 28

| | Tertiary Immune Response | |
|---|---|---|
| Group period | 2nd Week | 4th Week |
| 1 | 2 | 3 |
| 100 mcg SP-19 in physiological solution | 0 | 0 |
| 100 mcg SP-19 in CFA | 86020 (60214–111827) | 47291 (33103–61478) |
| 100 mcg SP-19 + PO | 22018 (15412–28623) | 15450 (10815–20085) |

TABLE 29

| Group period | Tertiary Immune Response | | | |
|---|---|---|---|---|
| | 1st Week | 2nd Week | 3rd Week | 4th Week |
| 100 mcg SP-22 in physiological solution | 0 | 0 | 0 | 0 |
| 100 mcg SP-22 in CFA | 278009 (194606–361411) | — | 158887 (111221–206553) | 97122 (67985–126258) |
| 100 mcg SP-22 + 700 mcg PO | 0 | 987 (691–1282) | 2122 (1486–2759) | 2705 (1893–3516) |

We claim:

1. A compound having immunostimulatory activity which is a polymer comprising subunits of the following formulae

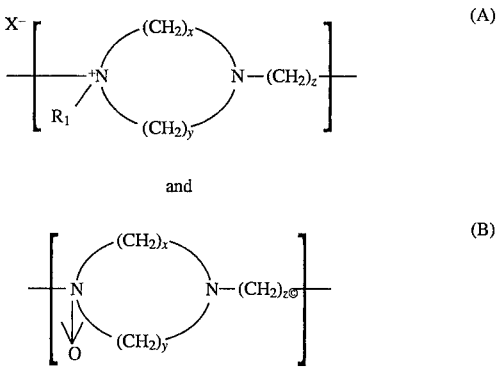

wherein $X^-$ is a pharmaceutically acceptable anion;

$R_1$ is substituted or unsubstituted $C_{1-16}$ alkyl, substituted or unsubstituted $C_{1-16}$ alkenyl or substituted or unsubstituted $C_{1-16}$ alkynyl, said $R_1$ substituents being selected from the group consisting of hydroxy, amino, substituted or unsubstituted $C_{6-10}$ aryl, $C_{1-16}$-alkylamino, di-$C_{1-6}$-alkylamino, carboxy, alkoxy carbonyl, carboxamido, cyano, $C_{1-6}$-alkoxy and halogen, said aryl group substituents being selected from the group consisting of hydroxy, amino, $C_{6-10}$ aryl, $C_{1-16}$-alkylamino, di-$C_{1-6}$-alkylamino, carboxy, alkoxy carbonyl, carboxamido, cyano, $C_{1-6}$-alkoxy, halogen, $C_{1-6}$ alkyl and $C_{1-6}$ haloalkyl;

x+y is an integer from 3 to 5;

z is an integer from 1 to 3;

x'+y' is an integer from 3 to 5 and may be the same or different as x+y;

z' is an integer from 1 to 3 and may be the same or different as z; and the ratio of A to B is from 1:9 to 9:1 said compound having immunostimulatory activity.

2. The compound according to claim 1 wherein $X^-$ is halogen.

3. The compound according to claim 1 wherein x+y is 4.

4. The compound according to claim 1 wherein x'+y' is 4.

5. The compound according to claim 1 wherein each of x, y, x' and y' is independently 2.

6. The compound according to claim 1 wherein z is 2.

7. The compound according to claim 1 wherein $R_1$ is $C_{1-16}$ alkyl, $C_{1-16}$ hydroxyalkyl or carboxy-$C_{1-5}$ alkyl.

8. The compound according to claim 1 wherein alkoxy carbonyl is $C_{1-4}$ alkoxy carbonyl.

9. The compound according to claim 1 wherein carboxamido is —C(=O)NH$_2$, —C(=O)NHNH$_2$, —C(=O)NH(CH$_2$)$_{1-10}$H or —C(=O)NH(CH$_2$)$_{1-10}$NH$_2$.

10. The compound according to claim 1 wherein the total number of subunits is between 310 and 2000.

11. The compound according to claim 1 wherein the ratio of A:B is not lower than 2:8.

12. A method of stimulating the immune response system of animals comprising administering to said animal a compound according to claim 1 in an amount effective to stimulate said immune response system.

13. The method of claim 12 comprising administering to said animal said compound which is conjugated to an antigen.

14. A vaccine for the propnylaxis and treatment of conditions requiring an enhanced immune response comprising the compound of claim 1 conjugated to an antigen.

15. The compound of claim 7 wherein $R_1$ is CH$_2$—COOH, $X^-$ is Br$^-$, the ratio of A to B is 3.5:6.5, and the number of subunits is 310.

16. The compound of claim 7 wherein $R_1$ is $C_2H_4$OH, $X^-$ is Br$^-$, the ratio of A to B is 9:1, and the number of subunits is 2000.

17. The compound of claim 7 wherein $R_1$ is $C_2H_5$, $X^-$ is Br$^-$, the ratio of A to B is 2:8, and the number of subunits is 1000.

18. The compound of claim ? wherein $R_1$ is $C_2H_5$, $X^-$ is Cl$^-$, the ratio of A to B is 9:1, and the number of subunits is 350.

19. The compound of claim 7 wherein $R_1$ is $C_4H_9$, $X^-$ is Br$^-$, the ratio of A to B is 1:1, and the number of subunits is 500.

20. The compound of claim 7 wherein $R_1$ is $C_6H_{13}$, $X^-$ is Br$^-$, the ratio of A to B is 4:6, and the number of subunits is 1000.

21. The compound of claim 7 wherein $R_1$ is $C_{16}H_{33}$, $X^-$ is Br$^-$, the ratio of A to B is 2:8, and the number of subunits is 500.

22. The compound of claim 7 wherein $R_1$ is $C_6H_{31}$, $X^-$ is I$^-$, the ratio of A to B is 8:2, and the number of subunits is 310.

23. The compound of claim 7 wherein $R_1$ is (CH$_2$)$_3$OH, $X^-$ is Br$^-$, the ratio of A to B is 8:2, and the number of subunits is 1800.

24. The compound of claim 7 wherein $R_1$ is (CH$_2$)$_4$OH, $X^-$ is Br$^-$, the ratio of A to B is 6:4, and the number of subunits is 1000.

25. The compound of claim 7 wherein $R_1$ is (CH$_2$)$_{16}$OH, $X^-$ is Br$^-$, the ratio of A to B is 3:7, and the number of subunits is 325.

26. The compound of claim 7 wherein $R_1$ is (CH$_2$)COOH, $X^-$ is Br$^-$, the ratio of A to B is 3.5 to 6.5, and the number of subunits is 2000.

27. The compound of claim 7 wherein $R_1$ is (CH$_2$)$_2$COOH, $X^-$ is Br$^-$, the ratio of A to B is 1:1, and the number of subunits is 1000.

28. The compound of claim 7 wherein $R_1$ is (CH$_2$)$_3$COOH, $X^-$ is Br$^-$, the ratio of A to B is 3:7, and the number of subunits is 500.

29. The compound of claim 7 wherein $R_1$ is $(CH_2)_4COOH$, $X^-$ is $Br^-$, the ratio of A to B is 3:7, and the number of subunits is 825.

30. The compound of claim 7 wherein $R_1$ is $(CH_2)_5COOH$, $X^-$ is $Br^-$, the ratio of A to B is 2:8, and the number of subunits is 400.

31. The compound of claim 8 wherein $R_1$ is $(CH_2)COOCH_3$, $X^-$ is $Br^-$, the ratio of A to B is 4:6, and the number of subunits is 2000.

32. The compound of claim 8 wherein $R_1$ is $(CH_2)_2COOCH_3$, $X^-$ is $Br^-$, the ratio of A to B is 3.5:6.5, and the number of subunits is 1000.

33. The compound of claim 8 wherein $R_1$ is $(CH_2)_5COOCH_3$, $X^-$ is $I^-$, the ratio of A to B is 3:7, and the number of subunits is 700.

34. The compound of claim 8 wherein $R_1$ is $(CH_2)COOC_2H_5$, $X^-$ is $Br^-$, the ratio of A to B is 1:1, and the number of subunits is 1000.

35. The compound of claim 8 wherein $R_1$ is $(CH_2)_2COOC2H_5$, $X^-$ is $Br^-$, the ratio of A to B is 4:6, and the number of subunits is 700.

36. The compound of claim 8 wherein $R_1$ is $(CH_2)_3COOC2H_5$, $X^-$ is $Br^-$, the ratio of A to B is 3.5: 6.5, and the number of subunits is 900.

37. The compound of claim 8 wherein $R_1$ is $(CH_2)COOC_4H_5$, $X^-$ is $Br^-$, the ratio of A to B is 4:6, and the number of subunits ms 1000.

38. The compound of claim 9 wherein $R_1$ is $(CH_2)CONHNH_2$, $X^-$ is $Br^-$, the ratio of A to B is 4:6, and the number of subunits is 2000.

39. The compound of claim 9 wherein $R_1$ is $(CH_2)_2CONHNH_2$, $X^-$ is $Br^-$, the ratio of A to B is 3:7, and the number of subunits ms 600.

40. The compound of claim 9 wherein $R_1$ is $(CH_2)CONH(CH_2)NH_2$, $X^-$ is $Br^-$, the ratio of A to B is 9:1, and the number of subunits is 800.

41. The compound of claim 9 wherein $R_1$ is $(CH_2)_2CONH(CH_2)NH_2$, $X^-$ is $Br^-$, the ratio of A to B is 4:6, and the number of subunits is 1500.

42. The compound of claim 9 wherein $R_1$ is $(CH_2)_2CONH(CH_2)NH_2$, $X^-$ is $Br^-$, the ratio of A to B is 3.5: 6.5, and the number of subunits is 1000.

43. The compound of claim 9 wherein $R_1$ is $(CH_2)CONH(CH_2)NH_2$, $X^-$ is $Br^-$, the ratio of A to B is 3:7, and the number of subunits is 800.

44. The compound of claim 9 wherein $R_1$ is $(CH_2)CONH(CH_2)NH_2$, $X^-$ is $Br^-$, the ratio of A to B is 2:8, and the number of subunits ms 1500.

45. The compound of claim 9 wherein $R_1$ is $(CH_2)CONH(CH_2)_6NH_2$, $X^-$ is $Br^-$, the ratio of A to B is 2:8, and the number of subunits is 2000.

46. The compound of claim 9 wherein $R_1$ is $(CH_2)CONH(CH_2)_8NH_2$, $X^-$ is $Br^-$, the ratio of A to B is 2:8, and the number of subunits is 750.

47. The compound of claim 9 wherein $R_1$ is $(CH_2)CONH(CH_2)_{10}NH_2$, $X^-$ is $Br^-$, the ratio of A to B is 4:6, and the number of subunits ms 450.

48. The compound of claim 9 wherein $R_1$ is $(CH_2)_5CONH(CH_2)NH_2$, $X^-$ is $Br^-$, the ratio of A to B is 4:6, and the number of subunits is 2000.

49. The compound of claim 9 wherein $R_1$ is $(CH_2)_2CONH(CH_2)_2NH_2$, $X^-$ is $Br^-$, the ratio of A to B is 1:1, and the number of subunits ms 1000.

50. The method of claim 12 wherein the compound is of the formula wherein $R_1$ is $(CH_2)COOH$, $X^-$ is $Br^-$, the ratio of A to B is 3.5:6.5, and the number of subunits is 310.

51. The method of claim 13 wherein the compound is of the formula wherein $R_1$ is $(CH_2)COOH$, $X^-$ is $Br^-$, the ratio of A to B is 3.5:6.5, and the number of subunits is 310.

52. The method of claim 14 wherein the compound is of the formula wherein $R_1$ is $(CH_2)COOH$, $X^-$ is $Br^-$, the ratio of A to B is 3.5:6.5, and the number of subunits is 310.

53. The method of claim 12 wherein said animal is human.

54. The method of claim 53 comprising administering to said human said compound which is conjugated to an antigen.

55. The method of claim 53 wherein the compound is of the formula wherein $R_1$ is $(CH_2)COOH$, $X^-$ is $Br^-$, the ratio of A to B is 3.5:6.5, and the number of subtraits is 310.

56. The method of claim 54 wherein the compound is of the formula wherein $R_1$ is $(CH_2)COOH$, $X^-$ is $Br^-$, the ratio of A to B is 3.5:6.5, and the number of subunits is 310.

* * * * *